US011137384B2

(12) United States Patent
Yoon et al.

(10) Patent No.: US 11,137,384 B2
(45) Date of Patent: Oct. 5, 2021

(54) RAPID AND NON-DESTRUCTIVE DETECTION OF INFECTION

(71) Applicant: Arizona Board of Regents on Behalf of the University of Arizona, Tucson, AZ (US)

(72) Inventors: Jeong-Yeol Yoon, Tucson, AZ (US); Robin E. Sweeney, Tucson, AZ (US)

(73) Assignee: Arizona Board of Regents on Behalf of the University Of Arizona, Tucson, AZ (US)

( * ) Notice: Subject to any disclaimer, the term of this patent is extended or adjusted under 35 U.S.C. 154(b) by 0 days.

(21) Appl. No.: 15/483,723

(22) Filed: Apr. 10, 2017

(65) Prior Publication Data

US 2017/0315108 A1    Nov. 2, 2017

Related U.S. Application Data

(60) Provisional application No. 62/320,093, filed on Apr. 8, 2016.

(51) Int. Cl.
*G01N 33/483* (2006.01)
*G01N 21/47* (2006.01)
*A61B 5/00* (2006.01)

(52) U.S. Cl.
CPC ....... *G01N 33/4833* (2013.01); *A61B 5/0075* (2013.01); *A61B 5/0077* (2013.01); *A61B 5/0082* (2013.01); *A61B 5/441* (2013.01); *G01N 21/47* (2013.01); *A61B 5/6898* (2013.01); *G01N 2021/4704* (2013.01); *G01N 2021/4711* (2013.01); *G01N 2021/4735* (2013.01); *G01N 2333/245* (2013.01); *G01N 2333/255* (2013.01); *G01N 2333/31* (2013.01); *G01N 2800/26* (2013.01)

(58) Field of Classification Search
None
See application file for complete search history.

(56) References Cited

U.S. PATENT DOCUMENTS

| 7,428,048 | B1 * | 9/2008 | Farkas | A61B 5/0059 356/364 |
| 2005/0141843 | A1 * | 6/2005 | Warden | G01N 15/14 385/141 |
| 2011/0117025 | A1 * | 5/2011 | Dacosta | A61B 5/0059 424/9.6 |
| 2014/0226772 | A1 * | 8/2014 | Watari | G21B 3/006 376/107 |

OTHER PUBLICATIONS

Banada Padmapriya P. et al., "Label-Free Detection of Multiple Bacterial Pathogens Using Light-Scattering Sensor," Biosensors and Bioelectronics 24, Sep. 11, 2008 (available online), pp. 1685-1692.
Cho Soohee et al., "Smartphone-Based, Sensitive mPAD Detection of Urinary Tract Infection and Gonorrhea," Biosensors and Bioelectronics 74, Jul. 11, 2015 (available online), pp. 601-611.

(Continued)

*Primary Examiner* — Jonathan Cwern
(74) *Attorney, Agent, or Firm* — Hylton-Rodic Law PLLC

(57) ABSTRACT

The invention relates to methods and devices to identify an infection via light scatter from a tissue surface.

12 Claims, 13 Drawing Sheets

(56) References Cited

OTHER PUBLICATIONS

Liang Pei-Shih et al., "Rapid and Reagentless Detection of Microbial Contamination Within Meat Utilizing a Smartphone-Based Biosensor," Scientific Reports, Aug. 5, 2014, pp. 1-9.
Park Tu San et al., "Smartphone Quantifies *Salmonella* From Paper Microfluidics," The Royal Society of Chemistry Publishing, Lab Chip, Oct. 3, 2013, pp. 4832-4840.
Tang Yanjie et al., "Light Scattering Sensor for Direct Identification of Colonies of *Escherichia coli* Serogroups O26, O45, O103, O111, O121, O145 and O157," PLOS ONE, vol. 9, Issue 8, Aug. 2014, pp. 1-15.
Singh Atul K. et al., "Laser Optical Sensor, a Label-Free On-Plate *Salmonella enterica* Colony Detection Tool," mBio, Jan./Feb. 2014, vol. 5, Issue 1, pp. 1-17.

\* cited by examiner

RAPID AND NON-DESTRUCTIVE DETECTION OF INFECTION

CROSS REFERENCE TO RELATED APPLICATIONS

This application claims the benefit of U.S. Provisional Application No. 62/320,093, filed on Apr. 8, 2016, entitled Rapid and Non-Destructive Detection of Wound Infection. The entirety of the foregoing is hereby incorporated by reference.

STATEMENT REGARDING FEDERALLY-SPONSORED RESEARCH

This invention was made with government support under Grant No. T32 HL007955, awarded by NIH. The government has certain rights in the invention.

FIELD OF THE INVENTION

The invention disclosed herein generally relates to methods and devices for identifying an infection via light scatter from a skin or wound surface.

BACKGROUND

Skin provides a barrier to pathogens. For instance, skin, both human and animal, is covered with bacteria continually [1-5]. Typically these bacteria are commensal, or healthy bacteria. When commensal bacteria become out of balance, or pathogenic species and strains of bacteria are added, an infection results [3, 5-7]. A skin infection typically results in a rash for healthy human and animal subjects, but can be limb or life threatening for some subjects [6-9]. Bacterial skin infections may cause disease states such as impetigo, cellulitis, abscesses, necrotizing fasciitis, and other severe health issues [8-11]. As the skin acts as a protective barrier to the body, any minor break in the skin combined with a skin infection can lead to deep tissue infections, bone infections, sepsis, and even death [6-7].

Anytime the surface of the skin is broken, there is also a risk of an infection. Generally, if noticed and treated quickly infection of a wound delays healing time, but is not life- or limb-threatening. If an infected wound goes unnoticed or untreated for a length of time, the wound can then become limb- and even life-threatening. In general, the sooner an infection is diagnosed and treated, the better the prognosis for the patient [12, 13, 14]. It is estimated that care for chronic wounds carries an economic burden of $6-$15 billion annually in the US, with infection of a chronic wound only increasing the cost of care [15] some studies suggest that the cost is truly as high at $25 billion annually [16].

Bacterial skin infections are a major concern with risk of community acquired infections as well as nosocomial infections [7, 17]. Risk factors that increase the likelihood of bacterial skin infections include diabetes, poor immune function (including immunocompromised patients or children with immature immune systems), use of immunosuppressive drugs, immobility, extended hospital stays, poor hygiene, and poor circulation to extremities [4, 6, 8-9, 11, 18].

Common bacterial species that cause skin infections include *Staphylococcus aureus*, *Streptococcus pyogenes*, *Pseudomonas aeruginosa*, and *Escherichia coli* [6-11]. A large diagnostic hurdle is the fact that many of these bacteria, particularly *S. aureus*, are commonly found on the skin as commensal bacteria [2-5, 19-21]. A major issue with common skin infections is the prevalence of antibiotic resistance in common pathogens, namely, *S. aureus*. Antibiotic resistance is a major health issue, with MRSA and VRSA (methicillin resistance *S. aureus* and vancomycin resistant *S. aureus*, respectively) being some of the biggest issues currently [7, 10, 20-21].

Knowing what bacteria are infecting a wound is critical in preventing the wound from becoming an extreme risk to the patient. Antibiotic treatment can differ based on the species of bacteria infecting the wound, gram stain of the bacterial species causing the infection, and severity of the wound [13]. Currently, to determine what bacterium is the cause of an infection a patient must see a physician who must initially suspect an infection based on inflammation and other observed factors, all of which are more subtle in the case of chronic wounds [13, 22]. Once infection is suspected the wound must be biopsied or swabbed, and the biopsy or swab must be cultured and gram stained, an invasive and painful process that takes days of valuable treatment time, access to a laboratory, and the additional cost of having a sample processed in a laboratory [12, 14, 22, 23]. Further complicating the process of an infection being noticed is the fact that while pain is a good indicator of infection, lack of pain is not a good indicator of lack of infection [23]. While samples are being analyzed for 1-3 days in a laboratory, patients are often prescribed broad-spectrum antibiotics, which can lead to increased antibiotic resistance in bacteria. If an infection is diagnosed early, when there is only one species causing the infection, and specifically, identifying that species, narrow-spectrum antibiotics can be used to treat the infection, but if it diagnosed late when the infection is polymicrobial, broad-spectrum antibiotics must be used to treat the infection, once again increasing the chance of drug resistance [13].

In diabetic patients specifically, the risk of a wound becoming infected is significantly increased due to compromised microvasculature and therefore poor immune response and wound healing. In the US alone, 9.3% of the population, or 29.1 million people, suffer from diabetes, resulting in an estimated $245 billion economic burden annually [24]. The CDC estimates that of these 29.1 million Americans, 15% will suffer from diabetic foot ulcers, which often lead to chronic wound infection. Of these patients with diabetic foot ulcers, an estimated 15-20% require lower extremity amputation as a result of infection [25]. Amputation can become necessary in diabetic patients because the chronic infection often becomes severe enough to cause osteomyelitis in bone nearby. *Staphylococcus aureus* is the most common pathogen found in diabetic foot ulcer infections and *E. coli* is the most common gram-negative pathogen found in these infections [23]. Diabetic foot ulcers are the primary reason for non-traumatic limb amputations in the US [12]. Studies have found that up to 28% of patients with diabetic foot ulcers require amputation [26] and others have reported that up to 96% of diabetic foot ulcer related amputations were preceded by infection [27]. Early detection of an infection and therefore early treatment can help to greatly reduce the rate of severe infections and limb amputations. As it stands, rates of infection this high are a huge burden to patients as well as to health care costs as well as increased hospitalization time and costs and patient quality of life.

The growing elderly population is another group at high risk for developing infections in chronic wounds. With age, both the innate and adaptive immune systems begin to decline in function. The inability of the immune system to function properly results in elderly patients experiencing delayed wound healing and therefore being at increased risk for infection [28]. There is concern that problems associated with age will only multiply as the population ages, with risk of wound infection being no exception.

Patients who have experiences traumatic burns are also at high risk of infection, which greatly increases morbidity and mortality. Gram-negative infections, namely E. coli, predominate in burn wounds and are a major determinant of morbidity and mortality [29]. In cases where a burn wound becomes infected, sepsis and multiorgan dysfunction occur as a result, leading to 75% of post-burn deaths being due to sepsis [30]. Further, in cases where burns are sustained, inflammation and immune suppression are associated with the initial injury, resulting in diagnosis being increasingly more challenging in these patients and antibiotic treatment less effective over time [29]. A physician being unable to easily distinguish between inflammation due to the injury and that due to infection presents and obvious need for a rapid, non-destructive device to diagnose infection early and often.

Surgical incisions are a large concern when considering risk of infection. It is estimated that 2-5% of surgeries result in surgical site infection (SSI) [31]. SSI's are major complications that are key in morbidity and mortality rates and can require further corrective surgeries [31, 32]. In 2000 alone, 71.5 million total surgeries were performed in the US, resulting in infection occurring in a huge number of patients at this rate [16]. SSI's do not only increase the chance of death, but also increase the economic burden of the procedure performed. In the case of surgery as well as lacerations sustained in general, location of the wound has been shown to increase or decrease the rate of infection, so monitoring these sites more closely with a less expensive and non-destructive device could prove to improve prognosis [32, 33].

A more ideal approach to treating a bacterial infection is through multiple, narrow-spectrum antibiotics specific to the species and strain of bacteria responsible for the infection, which is only possible once a pathogen has been identified [6, 8, 34]. Diagnostic methods using bacterial culture techniques can take significant amounts of time to determine a specific bacterial species and strain, resulting in a delay in the administration of optimal treatments. Reducing the time to specific diagnosis would reduce the time to specific and effective treatment, increasing the efficacy of these treatments and helping to slow the evolution of antibiotic resistant bacteria.

Currently the gold standard diagnostic measure for determining the specific bacterial species and strain responsible for a skin infection is bacterial culture using selective and differential media to determine the exact pathogen [7, 34]. Culture techniques take a minimum of many hours, but typically can take multiple days to specifically diagnose the nature and cause of an infection. In addition to the time required to diagnose patients via bacterial cultures, these techniques require trained staff, dedicated facilities, expensive equipment, and high reagent (media) costs. While waiting for the results of these diagnostic tests, patients are typically prescribed broad-spectrum antibiotics, which are known to heavily contribute to antibiotic resistance [20, 21].

While diagnosis through bacterial culture is the current gold standard, other methods have been developed in recent years. Genomic diagnostic techniques are commonly being used, such as gene amplification via polymerase chain reaction (PCR), or gene sequencing of DNA or 16s ribosomal RNA [1-2, 5, 35]. While these methods are effective at identifying specific bacterial species and even specific antibiotic susceptibilities or resistances, they are costly and time consuming. Mie scatter imaging systems, often called BARDOT (Bacterial Rapid Detection using Optical Scattering Technology) systems, have been used to identify bacterial species, but only following culture of the bacteria and not specifically for the purpose of diagnosing skin infection [36-38]. BARDOT systems not only require bacteria to be cultured before identification of the specific species is possible, but they require that bacterial colonies be on an optically transparent substrate, therefore making it impossible to translate this technology direction for use as a direct detection method from human skin [36-39]. All of these methods have similar issues in a clinical setting; they are time consuming, costly, and require specific (often expensive) laboratory equipment and a highly skilled staff.

A faster and more affordable approach to pathogen infection diagnosis is necessary to reduce health care costs as well as decrease time to treatment to increase efficacy of treatment across a wide variety of populations.

SUMMARY OF THE INVENTION

The instant invention relates to methods and devices for rapid and mobile diagnosis of an infected skin surface or a wound, as well as to determine the ability of the device to differentiate the pathogen such as the species of bacteria infecting a tissue sample.

Some embodiments of the invention relate to a device for analysis of one or more pathogens in or on a tissue where the device analyzes the tissue via Mie scattering.

In some embodiments, the tissue can be dermis, epidermis, an open wound, or any combination thereof.

In some embodiments, the one or more pathogens can be one or more species of bacteria, fungi, or viruses, or any combination thereof.

In some embodiments, the device employs a light source at an incident light angle relative to the tissue. In some embodiments, the device can be adapted to change the incident light angle. In some embodiments, the device can be adapted to analyze the tissue at one or more incident light angles.

In some embodiments, the light source is 650 nm red LED.

In some embodiments, photodiodes detect light scatter off of the tissue.

In some embodiments, detection can occur at multiple scatter angles from the tissue.

In some embodiments, the scatter angles are at least two angles in 10° increments from 10° to 80° relative to the tissue sample.

In some embodiments, analysis includes at least diagnosing an infection in the tissue and/or identifying one or more bacterial types in the tissue.

In some embodiments, a smartphone includes a source of light and/or conducts data collection and analysis.

Some embodiments relate to a method for diagnosing a tissue infection including the device where the method can include: placing a tissue in proximity to the device such that the photodiodes of the device are in suitable position with respect to the tissue to conduct a mie scattering determination; determining a mie scattering with the device; and comparing the mie scattering to a standard mie scattering; where difference in mie scattering is indicative of a tissue infection.

Some embodiments relate to a method for identifying one or more bacterial types in an infected tissue including the device where the method can include: placing a tissue in proximity to the device such that the photodiodes of the device are in suitable position with respect to the tissue to conduct a mie scattering determination; determining a mie scattering with the device; comparing the mie scattering to a standard mie scatterings, where specific mie scatterings correspond to a specific bacterial type.

BRIEF DESCRIPTION OF THE DRAWINGS

Those of skill in the art will understand that the drawings, described below, are for illustrative purposes only. The drawings are not intended to limit the scope of the present teachings in any way.

DETAILED DESCRIPTION OF THE INVENTION

Figure 1:
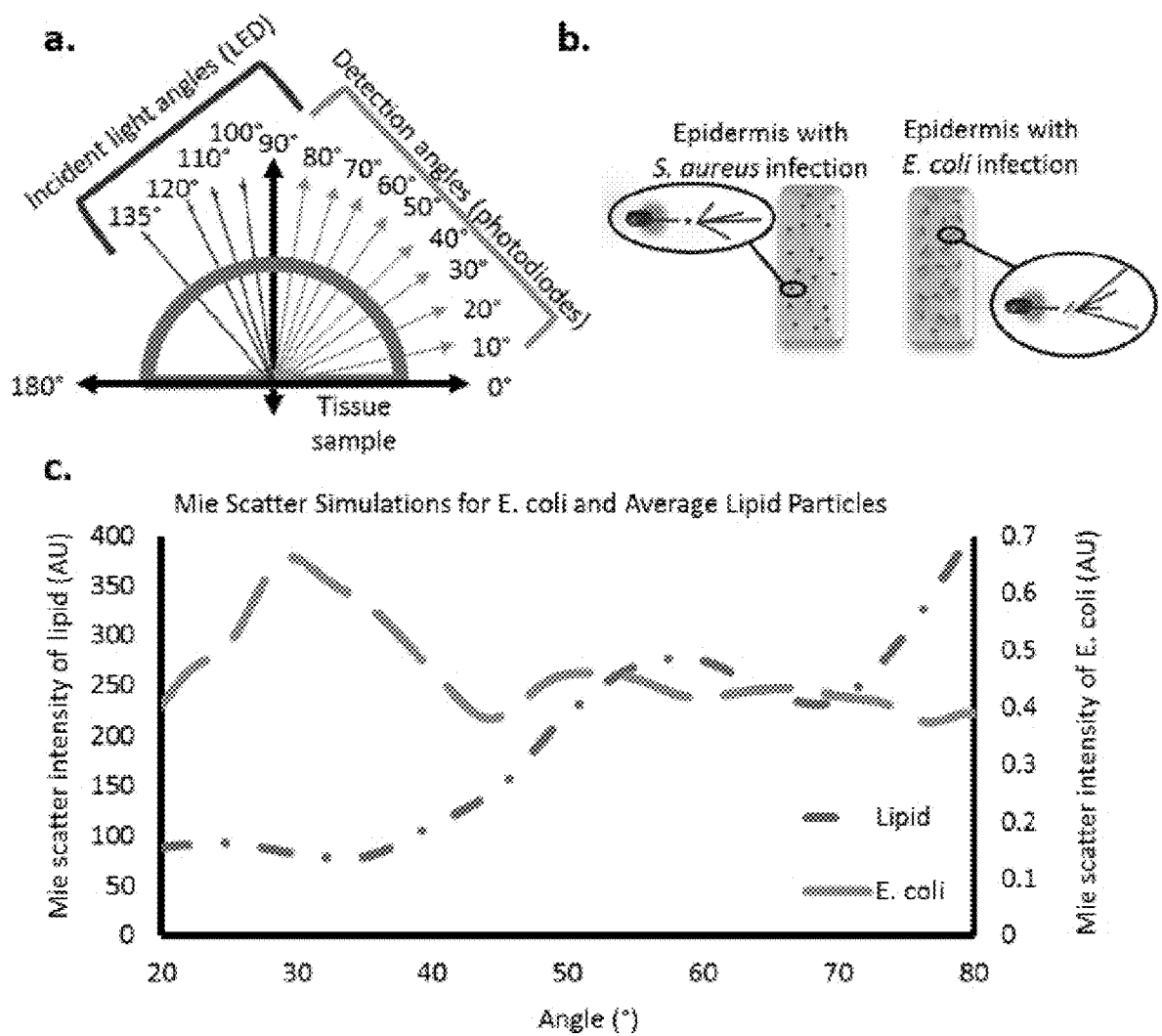
FIG. 1 is a schematic of an embodiment of the invention using Mie scatter spectra-based identification of bacteria. a) Definition of incident light and detection angles for an embodiment. All angles are defined relative to the tissue sample being placed on the plane from 0° to 180°. b) A schematic representation of the concept of different bacterial species generating unique Mie scatter spectra. Based on the size (r), shape, and refractive index (n) of the bacterial species, Mie scatter intensities will vary across a range of detection angles, with unique spectra being produced by each species. In this example, *Staphylococcus aureus*, small cocci, results in one unique Mie spectrum, while *Escherichia coli*, medium bacilli, results in its own unique Mie spectrum across a variety of angles. c) Mie scatter simulations conducted using the size and refractive index of *E. coli* versus those of typical lipid particles, much like those found in the skin. Simulations of Mie scatter trends show that *E. coli* can be distinguishable from lipid particles found within skin based on the use of a 650 nm light source resulting in a major peak at 30°.

The invention relates to embodiments of a portable and inexpensive device to diagnose infections. Embodiments of the invention can detect pathogens on a variety of surfaces such as agar, a porcine skin model, and on human skin. Also within the embodiments of the invention are methods of such detection. The pathogen can be bacterial, viral, fungal, or the like, or any combination thereof.

In some embodiments, the device includes a novel angular photodiode array that can detect species-specific bacterial infections on tissue samples. With the invention, bacterial species that have different shapes, sizes, and Gram stains (and thus refractive indices) show unique trends across various angles of detection. Information obtained from the device can determine if an infection is present, and, if so, the responsible bacterial species and therefore the ideal initial antibiotic treatment. Common skin contaminants (e.g., body lotion) have little to no impact on the Mie scatter spectra from tissue samples.

In some embodiments, the device employs Mie scatter, or the Mie solution to Maxwell's equation, as an effective method to immediately detect a bacterial contamination in various matrices [40-42]. Mie scatter is dependent on particle size and concentration, and changes here result in changes in scatter patterns across a variety of angles [41]. Embodiments of the invention take advantage of these changes in Mie scatter patterns based on particle size and concentration to detect bacterial infections on tissue surfaces and determine the bacterial species responsible for the infection.

In previous methods, Mie scatter "images" have been collected and analyzed, which were captured at a certain fixed angle. In some embodiments, the invention does not collect any images, but rather collects the Mie scatter intensities over a range of scattering angles. Mie scatter imaging differs from the technique used here in that it uses forward scatter patterns through agar from colonies grown on the surface to identify patterns [43]. These systems, often referred to as BARDOT systems, require bacteria to be swabbed and cultured on agar before identification of bacterial species [44-46]. The invention differs in that backscatter can be detected from a tissue surface rather than forward scatter detected through agar, meaning that swabbing and culturing a bacterial contamination is not necessary.

In some embodiments, the invention relates to Mie scatter spectra to directly detect infection on animal and human skin. Mie scatter spectra are defined here as the collection of photodiode readings at eight different detection angles. Mie scatter patterns can be collected across a variety of incident light angles (for example, five different angles from the surface of each tissue sample). Mie scatter is dependent on particle size, morphology, refractive index, and concentration. Changes in these factors due to bacterial growth and interactions with tissue components, especially lipids, result in changes in scatter patterns across a variety of angles [47]. The invention takes advantage of changes in Mie scatter spectra based on these factors. The invention can utilize Mie scatter spectra collected from various skin samples to rapidly detect bacterial infections on tissue surfaces and determine the bacterial species responsible for the infection. Unlike other Mie scatter-based biosensing techniques, such as the use of Mie scatter intensities at fixed angle to detect bacterial presence through particle immunoagglutination, this method does not require sample processing, additional reagents, or bioreceptor use, which eliminates time and labor for lengthy reagent and sample preparation [48-49].

In some embodiments, the device includes a custom stage that is developed to monitor Mie backscatter from a surface from a light source. The surface can be a tissue surface. In some embodiments, the light source can be any red color from 600-700 nm. For example, the light source can be any light source that either is or can be filtered to be 650 nm in wavelength. For example, the light source can be 650 nm LED. In some embodiments, Mie scatter is detected at increments of 10° from 100° to 80° using this device. In other embodiments, a continuous range of angles can be employed and/or a selection of any angle or combination of angles can be employed. With the benefit of the present disclosure, a person of ordinary skill in the art will be able to identify suitable angles and/or wavelengths of light in order to adapt the invention to a particular use for detection of a pathogen and/or distinction between two or more pathogens. In some embodiments such detection and/or distinction is intended to be qualitative, while in others it is intended to be quantitative. Mie scatter simulations can be carried out to show changes in scatter patterns based on changes in particle size and concentration.

In some embodiments, the device includes a photodiode array suspended above the stage. In some embodiments, the photodiode array is in an arc above the stage. In addition to collecting data in a 90° arc as depicted in FIG. 1, some embodiments include a device employing photodiodes across a 180° half circle with the light placed perpendicular to the sample, where data are collected against the full 180° arc. In another embodiment, a device employs photodiodes at any selected point on a half sphere above the sample such that the light source is placed perpendicular to the sample in the half sphere. In some embodiments, the device includes two, three, four, five, six, seven, eight, nine, or ten or more photodiodes.

In some embodiments, the incident angle of the light source can be adjusted. The light can be positioned at different angles relative to the tissue. The tissue can be analyzed at each of the different incident angles. For example, the light can be positioned at angles of 90°, 100°, 110°, 120°, and 135°, relative to the tissue surface. In other embodiments, other angles can be used, as optimized by the user in view of the pathogen to be identified or pathogens to be distinguished, as well as in view of other factors relevant to the selection of parameters to be employed.

In some embodiments, principal component analysis (PCA) is used as a statistical method to create a predictive model of the species of bacterial infection on the surface of the skin or a wound. PCA is used by creating a predictive model with tissue samples with known inoculations, which can later be used to predict the pathogen responsible for an infection on an unknown sample.

In some embodiments, the circuit design is a series of two gain stages attached to each of 8 photodiodes, with the amplified output being read and collected by an Arduino Mega 2560. The circuit can be simplified to contain a single gain stage or be a printed circuit board. The circuit can also be modified to use other light collectors, such as photomultiplier tubes or similar, rather than photodiodes.

In some embodiments, the invention relates to a novel device that is able to detect Mie scatter spectra from a tissue surface using a light source, for example an LED, a plurality of photodiodes, for example eight photodiodes, and an angular array, for example a 3D-printed angular array. The device is able to detect the presence or absence of a bacterial infection on dermis and can specifically diagnose the pathogen responsible for the infection. The device simplifies and expedites the diagnosis of bacterial wound infection and decreases time to specific treatment Is some embodiments, the device can include an attachment to a smartphone, tablet, or computer to feed signal from the photodiodes directly to the smartphone. The device can include a smartphone or tablet that collects light scatter via the camera.

In some embodiments, the device is small enough to accommodate a tissue sample.

In some embodiments, the device is enlarged to be capable of accommodating a sample as large as a human foot, or larger. In some embodiments, a patient can place his/her foot on a stage and determine if he/she has an infection and if so what bacterium is causing the infection in seconds and without any physical contact to the patient. The device can be enlarged to accommodate any body part without a stage, by aligning the focal point with the point of interest on the patient.

In some embodiments, the device is capable of detecting the presence of an infection and the bacteria responsible for the infection without physically contacting a sample. The device can detect the presence of an infection and the infecting bacteria rapidly. For example, within 10, 5, 3, 2, or 1 seconds, or less.

In some embodiments, photodiode (PD) readings are collected every 250 ms and averaged over three seconds (12 data points per PD angle at each LED angle at each of three location on a sample, 1,440 data points per tissue sample). These readings can be collected as the average of any number of data points, collected at a faster or slower rate than in this example.

In some embodiments, Mie scatter simulations including the following parameters were used: particle radius (r)=10 μm, refractive index (n)=1.46, refractive index of medium (water)=1.33, wavelength=650 nm, and size distribution assumed to follow a normal distribution with 10% standard deviation. In other embodiments, the following parameters were used [47, 49]: particle radius (r)=2.5 μm (hydrodynamic dimensions of 5 μm×1 μm), refractive index (n)=1.40, refractive index of medium (water)=1.33, wavelength=650 nm, and size distribution assumed to follow a normal distribution with 10% standard deviation. Similar Mie scatter simulations can be conducted for any bacterial species, based on the size and refractive index of the particular bacterial species.

In some embodiments, the device can determine the type of bacteria. For example, the device can identify gram-negative bacilli bacterial species (*E. coli*) or gram-positive cocci bacterial species (*S. aureus*). The device can identify

*S. aureus, Pseudomonas aeruginosa, Streptococcus pyogenes*, and *E. coli* which are some of the most common pathogens in skin infection; these bacteria differ in size, shape, and Gram stain, and therefore they likewise differ in refractive index. Any bacteria that differ in size, shape, and Gram stain, and hence differ in refractive index, can be detected with the device.

In some embodiments, the device can detect non-bacterial pathogens including fungal species and viral species. Fungi, viruses, and virus-like particles have distinctive light-scattering properties that are amenable to application of the concepts and approaches disclosed herein. Hence in some aspects and embodiments of the invention, an infection of the skin or a wound can be analyzed via Mie scattering to detect presence or absence of one or more species of fungus or virus, and to distinguish between or among multiple possible pathogens. The techniques disclosed here, for varying angles and wavelengths of the light source and of the detected light, and for analyzing the data produced therefrom, can be used for these non-bacterial pathogens, and/or for combinations of bacterial and non-bacterial pathogens.

In some embodiments, the instant invention relates to the detection of Mie scatter patterns by a mobile device. The mobile device can be a smartphone camera or an angular photodiode array attachment for a smartphone. For example, an application is made to use a smart phone to detect the same angular scatter pattern. The use of photodiodes at specified angles means that this device can be replaced by the use of a smartphone camera in the same angular pattern with an application designed to analyze data from the scatter detected by the camera. Patients can simply use their own smartphone to scan a wound periodically to monitor infection. Data analyzed by the application can notify the patient to see a physician and can notify the physician of the results prior to their visit. The device and smartphone application can also be especially important in areas with limited access to healthcare facilities and professionals. Remote monitoring of a wound can allow patients who are simply unable to go to a physician, do not have access to a laboratory, and do not have the funds needed to carry out culture-based diagnosis to greatly benefit from a simple, rapid, inexpensive, and mobile device to monitor wound infection. The device can warn patients of an infection without the delays currently caused by the time it takes for a patient to notice an infection, then get to a physician despite limited mobility and pain, and then await results from laboratory testing, especially in cases where infection is difficult to distinguish from response to an injury. The patient and physician can be notified early of an infection and the cause of the infection through mobile monitoring of a wound, so that the time to effective treatment is greatly decreased and prognosis as well as quality of life is improved for these patients. Mobile monitoring allows early notification of infection to a patient and a physician to allow early treatment and, therefore, improved efficacy of treatment, prognosis, and quality of life. Rapid optical analysis of a wound surface eliminates the need for any reagents, lengthy assay times, tedious sample handling, and the need for access to skilled technicians in a laboratory.

The device can determine the presence of an infection and the species of bacteria responsible for the infection. Immediate and specific diagnosis of the species of infection can reduce the need for the use of broad spectrum antibiotics, which contribute greatly to antibiotic resistance, instead allowing for the use of narrow spectrum antibiotics. The use of this device can bypass the initial steps of identifying the bacteria responsible for the infection, instead allowing for specific culture and genetic tests on resistance to be carried out immediately.

EXAMPLES

The following non-limiting examples are provided to further illustrate embodiments of the invention disclosed herein. It should be appreciated by those of skill in the art that the techniques disclosed in the examples that follow represent approaches that have been found to function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

Example 1

Materials and Methods

Study Design

Figure 2:
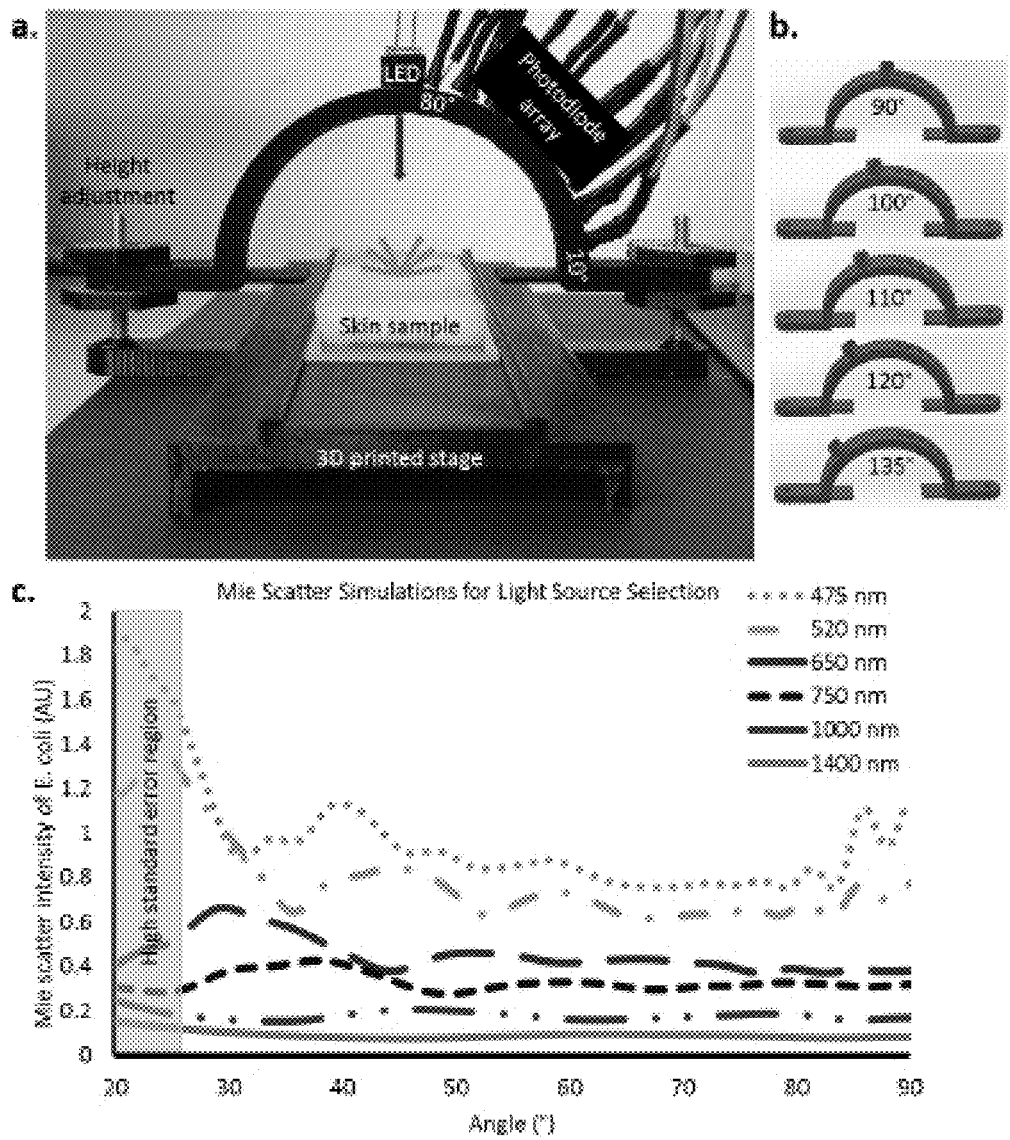
FIG. 2 depicts an example experimental setup using an embodiment of the invention. Experimental design was based off of detecting two species of pathogenic bacteria from three surfaces. Lysogeny broth-Miller (LB-Miller) was used a control to directly compare to inoculations of bacteria in the same media. *E. coli, S. aureus*, and the sterile LB control were individually inoculated on each of three surfaces, LB agar plates, porcine epidermis, and human cadaveric epidermis. While the schematic representations shows that all samples had only the bacteria added via inoculation on them, porcine epidermis and human epidermis both have natural, commensal bacteria on their surfaces, but LB agar is sterile and should contain no additional bacteria on the surface.

Study groups in this controlled laboratory experiment included *Escherichia coli, Staphylococcus aureus*, and a control of sterile LB-Miller medium on three surfaces; LB-Miller agar, porcine epidermis, and human cadaveric epidermis (FIG. 2). Mie scatter spectra were collected using a custom angular photodiode array at 10° increments from 10° to 80° (FIG. 3a). Each sample was analyzed at three separate locations for a representative collection of scatter from an entire surface. Each of the three locations was analyzed with the LED light source at 5 different angles relative to the surface; 90°, 100°, 110°, 120°, and 135° (FIG. 3b). Samples were randomly assigned an inoculum and researchers were not blinded.

Bacteria Solutions

*Escherichia coli* K12 (Sigma-Aldrich, St. Louis, Mo., USA) and *Staphylococcus aureus* (ZeptoMetrix, Buffalo, N.Y., USA) were individually cultured in lysogeny broth (LB) Miller's formula (Molecular Biologicals International Inc, Irvine, Calif., USA) at 37° C. for 8 hours. Bacteria were freshly cultured prior to each experiment. All bacterial cultures were grown to maximum concentration ($10^8$ CFU/mL). Concentration was determined through serial dilution and plate counting. Sterilized LB was used as a control to directly compare to bacteria grown in the same broth.

Bacteria Cultures on Agar

Freshly grown cultures were plated on LB-Miller agar plates (BIO5 Media Facility, Tucson, Ariz., USA) by uniformly spreading 400 µL of a bacteria culture across the surface as a puddle to avoid texture due to introducing an inoculating loop or needle. Cultured agar was cut to approximately 1.5 cm by 5 cm after 8 hours of incubation at 37° C. and placed on microscope slides with care taken to avoid disrupting the surface of the agar. Pure bacteria cultures on agar were analyzed using the photodiode array described.

Porcine Skin

Porcine skin (University of Arizona Food Products and Safety Laboratory, Tucson, Ariz., USA) was acquired immediately following slaughter. Hair was shaved from the skin surface, exposing the epidermis. Samples were washed with water to remove excess dirt and cut into approximately 1.5 cm by 5 cm rectangles. Samples were then randomly divided into experimental groups and inoculated with 150 µL of either *E. coli, S. aureus*, or sterile LB-Miller medium, all of which were spread evenly across the surface of the skin with an inoculating needle. Samples were sealed with Parafilm M (Bemis Flexible Packaging, Oshkosh, Wis., USA) in individual petri dishes and incubated for 8 hours to allow bacterial growth on the sample.

Rather than bacterial inoculation, alternative porcine dermis samples were coated with body lotion (St. Ives Skin Renewing Collagen Elastin, Unilever, Englewood Cliffs, N.J., USA), a common skin contaminant. Preparation and analysis of lotion coated skin samples was identical to that of bacteria inoculated samples, with the exception of inoculum.

Human Cadaveric Skin

Human cadaveric skin was acquired following a period of deep freeze from the ankle region of one male individual. Cadaveric skin samples were prepared into identical samples as porcine skin. The epidermis remained intact for all samples, but excess hair was shaved from the surface where necessary. Samples were allowed to rest at room temperature following inoculation of 150 µL of E. coli, S. aureus, or LB (Miller) broth before analysis. Human skin samples were not incubated as porcine skin samples were due to the melting temperature of the lipids in the human skin, instead, bacteria were allowed to adjust to the surface during a 15-minute resting period. All experiments with human cadaveric skin samples were performed in accordance with relevant guidelines and regulations. Since these samples were cadaveric tissues, approval by the institutional review board of the University of Arizona was waived. All samples were from the willed body program at the University of Arizona College of Medicine.

Selective and Differential Culture Plating

To show that the inoculated bacteria did in fact survive and grow on the tissue surfaces, following inoculation and growth of bacteria, skin surfaces were stamped on selective and differential agar plates to identify bacteria. Eosin methylene blue (EMB) agar (Hardy Diagnostics, Santa Maria, Calif. and Springboro, Ohio, USA) was used to identify E. coli, based on the growth of E. coli as black with a green metallic sheen on this agar. Both blood agar (BIO5 Media Facility, Tucson, Ariz., USA) and mannitol salts agar (Hardy Diagnostics, Santa Maria, Calif. and Springboro, Ohio, USA) were used to identify S. aureus, based on the growth of this bacterium with a distinguishable hemolysis on blood agar and the survival of this bacterium on mannitol salts agar and turning the agar yellow through this growth.

Mie Scatter Detector

Directly following incubation of tissues, samples were placed on a standard microscope slide with care taken to not disrupt the surface of the skin. A 3D printed stage held the microscope slide in a fitted channel to be analyzed by a custom photodiode array. A 650 nm red LED light source illuminated the tissue with an array of PIN photodiodes detecting scatter off of the tissue sample at 10° increments from 10° to 80° relative to the tissue surface (FIG. 3a). The incident light angle was changed with each tissue sample being analyzed at each of five incident angles; 90°, 100°, 110°, 120°, and 135° (FIG. 3b). All photodiodes were used in photovoltaic mode (optimum mode for PIN PDs) and connected to LM324 quad op-amps to amplify current outputs. Amplified signals were sent to the analog inputs of an Arduino Mega 2560 microcontroller, providing an angular spectrum. Array height was adjusted prior to each measurement, so the array was level with the surface of each tissue sample.

Data Collection

Each tissue sample was analyzed at three different locations. Photodiode (PD) readings were collected every 250 ms and averaged over three seconds (12 data points per PD angle at each LED angle at each of three location on a sample, 1,440 data points per tissue sample). For each sample location and LED angle, photodiode readings were averaged at each angle, and standard error of the average of each 3 s reading was calculated over three different tissue locations of multiple samples for the purpose of error bars.

Mie Scatter Simulation

Mie scatter simulations were carried out using MiePlot v4.2.11. For lipids, the following parameters were used (Liang et al., 2014): particle radius (r)=10 µm, refractive index (n)=1.46, refractive index of medium (water)=1.33, wavelength=650 nm, and size distribution was assumed to follow a normal distribution with 10% standard deviation. For individual E. coli, the following parameters were used [47, 49]: particle radius (r)=2.5 µm (hydrodynamic dimensions of 5 µm×1 µm), refractive index (n)=1.40, refractive index of medium (water)=1.33, wavelength=650 nm, and size distribution was assumed to follow a normal distribution with 10% standard deviation. To determine the appropriate light source for the device, simulations were conducted based on E. coli, varying only wavelength of the light source from 475 nm to 1400 nm.

Data Analysis

Data were initially analyzed using Microsoft Excel. Data were normalized to the control group (LB inoculation) by subtracting the average over 3 s of PD readings at each angle of the control from that of the experimental group. The goal in doing this was to eliminate noise due to commensal bacteria present on the skin prior to bacterial inoculation (infection). Data were then plotted within the program to display differences caused by the inoculation of bacteria on the sample. Student t-test assuming unequal variance was used to determine statistical significance with $p<0.05$ being considered significantly different.

Data Analysis (PCA)

Due to the complex interactions between bacteria and the many cells types and macromolecules present in porcine and human skin, data collected from both skin types were further analyzed using principle component analysis (PCA). The Unscrambler v9.7 was used for PCA of the average of 12 PD readings averaged over three locations on each sample at each angle for each of five LED angles. Student t-test assuming unequal variance was used to determine statistical significance with $p<0.05$ being considered significantly different.

Example 2

Device Design

A device design is shown in FIG. 3a. A semi-circular angular array was 3D printed with insertion points for an LED and a series of PIN photodiodes (PDs). The array was attached to a 3D stage, designed to fit a standard microscope slide, in a manner that would allow adjustment of array height relative to the stage.

The angular array was designed to have insertion points for PDs at 10° increments from 10° to 80° and a single insertion point for an LED at either 90°, 100°, 110°, 120°, or 135°. Five arrays were designed to each hold the LED at a single angle due to space constraints. In another embodiment a single array to accommodate variable LED positions is employed (FIG. 3b).

Following Mie scatter simulations (using MiePlot v4.2.11) a 650 nm red LED was used as a sole light source (FIG. 3b). Mie scatter simulations were performed for *E. coli* at wavelengths of 475 nm, 520 nm, 650 nm, 750 nm, 1000 nm, and 1400 nm (FIG. 1b). Wavelengths in the ultraviolet (UV) range were not considered due to their bactericidal capability and dangers of UV exposure to human skin. Side scatter results in large variability in data collected at 10° and 20°, due to the presence of hair follicles and imperfections in the topography of tissue samples. Light sources at 475 nm and 520 nm were not considered due to the major peaks of 21° and 24° (where noisy side scatter should be used), respectively. NIR wavelengths (750 nm, 1000 nm, and 1400 nm) were also ruled out due to relative low intensity major peaks and that the eventual goal of translation to smartphone would require an additional NIR light source. A 650 nm LED light source was selected based on a high intensity major peak at 30°, which avoids variability at low angles of detection, the designed device is able to detect this peak with a PD.

Example 3

Identification of Bacteria in Pure Culture

Using the Materials and Methods in Example 1 and device of Example 2, bacteria grown on agar plates were tested using the designed photodiode array shown in FIG. 3a to determine if pure cultures of *E. coli* differed from those of *S. aureus*. Significant differences were detected between Mie scatter spectra across a variety of incident light angles of these two bacterial species grown on LB-Miller agar despite no obvious visual differences between cultures on agar (FIG. 4). Mie scatter spectra at each incident angle differ and, at each angle, significant differences exist between *E. coli* and *S. aureus* at every incident light angle. Significant differences ($p<0.05$) were found between *E. coli* vs. control samples (marked *), *S. aureus* vs. control samples (marked *), and *E. coli* vs. *S. aureus* samples (marked †) (FIG. 4).

Example 4

Identification of Bacteria on Porcine Epidermis

Figure 5:
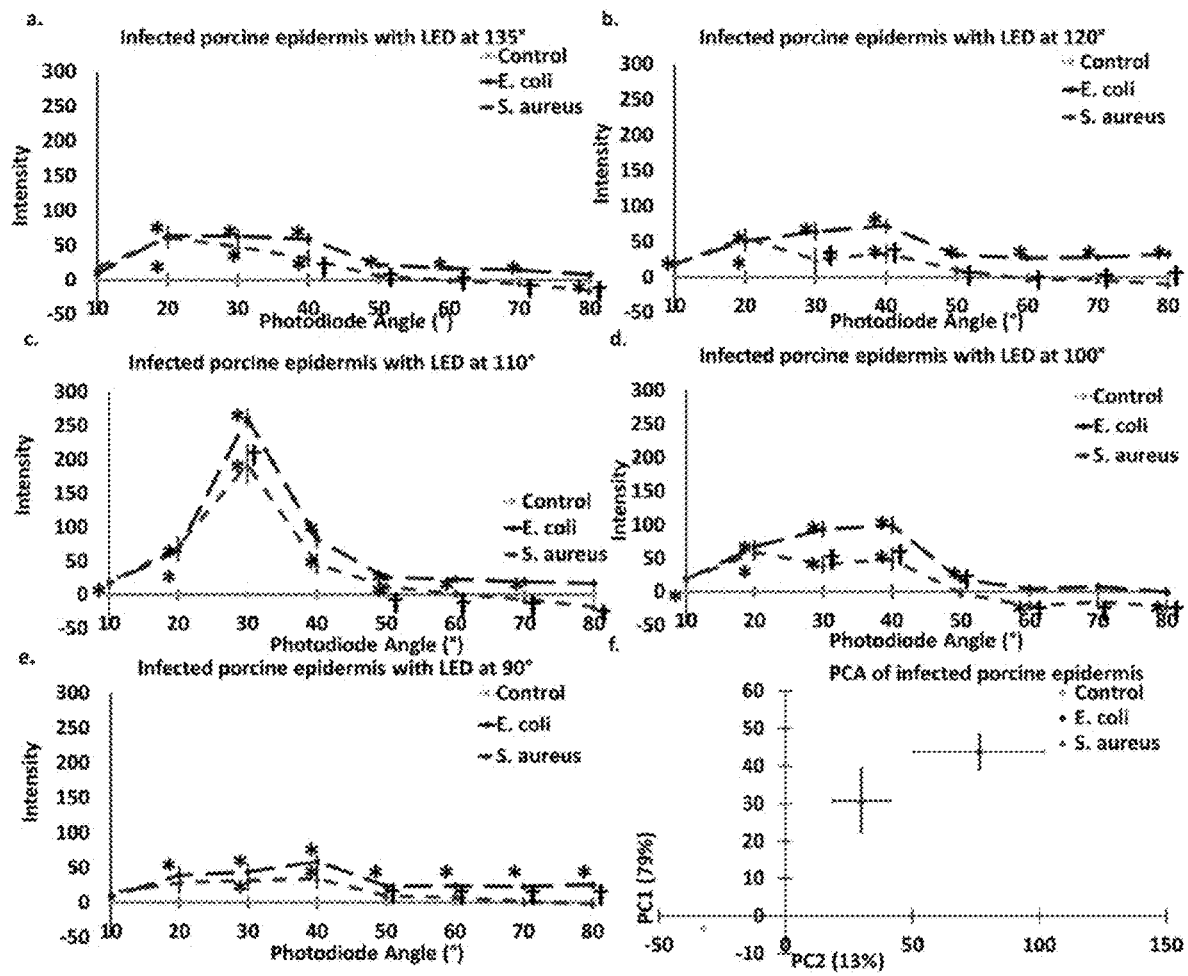
FIG. 5 depicts an example of identification of bacteria on a porcine epidermis model using an embodiment of the invention. a-e) Data obtained from the photodiode array designed by scanning porcine epidermis samples inoculated with sterile LB, *E. coli*, or *S. aureus*. Incident light angle was changed for each of the five data sets; 135° (a), 120° (b), 110° (c), 100° (d), and 90° (e). At each individual incident light angle, significant differences result between bacterial inoculation and control samples as well as between each species of inoculation; *E. coli* or *S. aureus*. The trend changes as the incident light angle changes, and distinct differences are maintained despite changing trends with changing incident angles. One data point is considered to be the average of 12 readings from each photodiode (3 s scan). f) Principle component analysis (PCA) of the data shown in a-e shows distinct differences between infections of the porcine epidermis with *E. coli* vs. *S. aureus* vs. only the commensal bacteria present on control samples. The two principle components shown, PC1 and PC2, account for 92% of the data shown in a-e, 79% and 13% for PC1 and PC2, respectively. Each of five porcine epidermis samples was scanned at three unique locations for 3 s at each location. Error bars represent standard error of the mean, the control group in f has standard error of zero. * is shown to the left side of each data point indicating significant difference ($p<0.05$) between *E. coli* vs. control samples or between *S. aureus* vs. control samples. † is shown to the right side of each data point indicating significant difference ($p<0.05$) between *E. coli* vs. *S. aureus* samples.

Using the Materials and Methods in Example 1 and device of Example 2, porcine epidermis samples inoculated with *E. coli* showed significantly different Mie scatter spectra than those inoculated with *S. aureus* ($p<0.05$, marked †), despite the presence of natural, commensal bacteria on all porcine epidermis samples (FIG. 5;). Mie scatter spectra between these species consistently differed across all incident light angles using the developed device (FIG. 5a-e). Significant differences ($p<0.05$) were found between *E. coli* vs. control samples (marked *), *S. aureus* vs. control samples (marked *), and *E. coli* vs. *S. aureus* samples (marked †) (FIG. 5).

To summarize differences between Mie scatter spectra produced by each species, principle component analysis (PCA) (FIG. 5f) was carried out on the data shown in FIG. 5a-e. There are 40 dimensions (8 detection angles and 5 incident angles) in raw Mie scatter spectra. FIG. 5a-e shows the mean Mie scatter intensities of 15 data points (five samples each at three different locations) for each given combination of incident and detection angle. PCA was conducted for each assay, not for the average values, and the mean principal component (PC) values with the standard errors were plotted on the PCA score plot. Using two principle components 92% of the data obtained was useful in explaining differences between the experimental groups (PC1 accounts for 79% of data, PC2 accounts for 13% of the data). Data obtained from an incident light angle of 110° were excluded from PCA due to the outlier effect the significantly higher magnitude of intensity at this angle (FIG. 5c). Significant differences ($p<0.05$) exist between the presence of additional bacteria (an infection) and natural, commensal bacteria, as well as the two species of bacterial infections tested. Through PCA, significant differences were shown ($p<0.05$) between PC1 for *E. coli* vs. that for control samples as well as for *S. aureus* vs. that for control samples.

Example 5

Identification of Bacteria on Human Cadaveric Epidermis

Using the Materials and Methods in Example 1 and device of Example 2, human cadaveric epidermis inoculated with *E. coli* showed significantly different Mie scatter spectra than those inoculated with *S. aureus* on human cadaveric epidermis samples ($p<0.05$, marked †), again, despite the presence of commensal bacteria on the skin. Mie scatter spectra differed between each inoculated species of bacteria and between the presence of infection and presence of only commensal bacteria, shown through control group of sterile LB inoculation ($p<0.05$, marked *) (FIG. 6a-e). Error bars show standard error of the mean.

Figure 6:
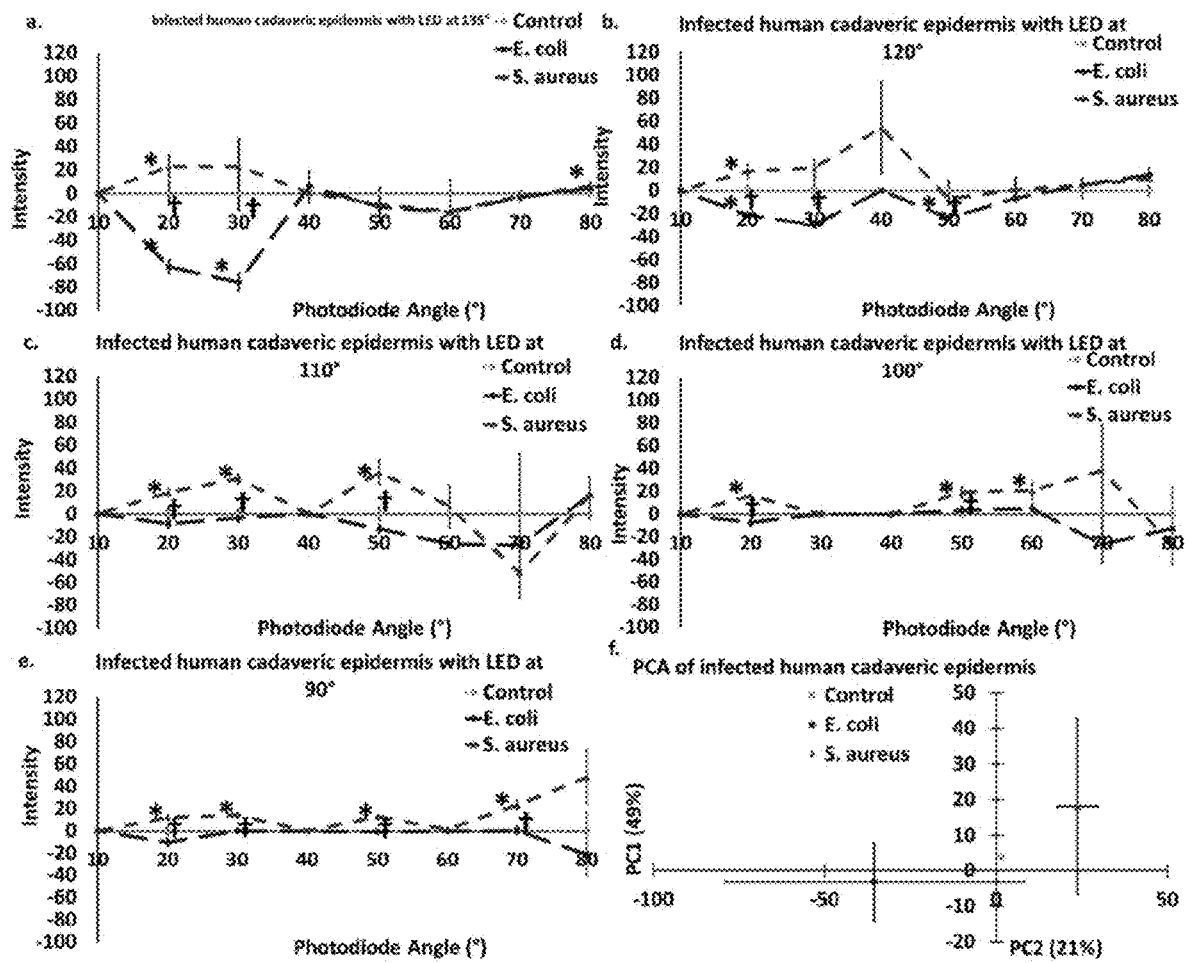
FIG. 6 depicts an example of identification of bacteria on a human cadaveric epidermis using an embodiment of the invention. a-e) Data were obtained from the photodiode array designed by scanning human cadaveric epidermis samples inoculated with sterile LB, *E. coli*, or *S. aureus*. Incident light angle was changed for each of the five data sets; 135° (a), 120° (b), 110° (c), 100° (d), and 90° (e). At each individual incident light angle, significant differences result between bacterial inoculation and control samples as well as between each species of inoculation; *E. coli* or *S. aureus*. The trend changes as the incident light angle changes and distinct differences are maintained despite changing trends with changing incident angles. One data point is considered to be the average of 12 readings from each photodiode (3 s scan). f) Principle component analysis (PCA) of the data shown in a-e shows distinct differences between infections of the human cadaveric epidermis with *E. coli* vs. *S. aureus* vs. only the commensal bacteria present on control samples. The two principle components shown, PC1 and PC2, account for 70% of the data shown in a-e, 49% and 21% for PC1 and PC2, respectively. Adding an additional PC, PC3 would account for an additional 14% of the data shown in a-e. Each of 2 human cadaveric epidermis samples was scanned at three unique locations for 3 s at each location. Error bars represent standard error of the mean, the control group of f has standard error of zero. * is shown to the left side of each data point indicating significant difference ($p<0.05$) between *E. coli* vs. control samples or between *S. aureus* vs. control samples. † is shown to the right side of each data point indicating significant difference ($p<0.05$) between *E. coli* vs. *S. aureus* samples.

Again, to summarize differences between Mie scatter patterns produced by each bacterial species, PCA was carried out (FIG. 6f). In this instance, PC1 and PC2 accounted for 70% of data (49% and 21%, respectively). The introduction of a third dimension here, PC3, would account for a further 14% of the data. Significant differences ($p<0.05$) are shown between both infected and control samples and each species of bacteria infecting the human cadaveric skin surface, *E. coli* and *S. aureus*, although the standard error is larger than those from porcine skin data.

Example 6

Lack of Interference by Common Skin Contaminants

Figure 8:
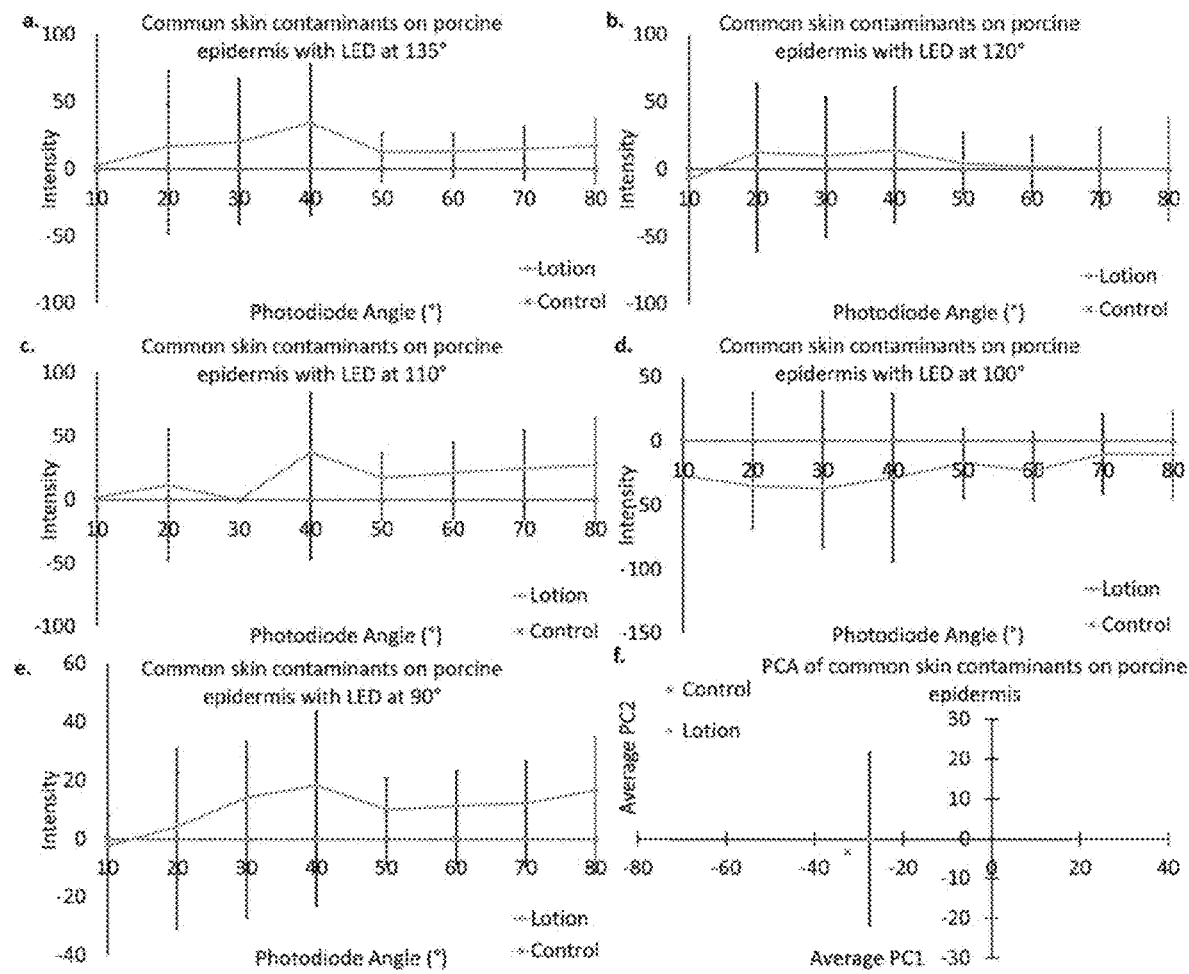
FIG. 8 depicts experiments showing that common skin contaminants were not detected by an embodiment of the invention.

Using the Materials and Methods in Example 1 and device of Example 2, an inoculation of body lotion was used to determine the ability of the designed device to detect only bacteria presence, rather than the presence of non-bacterial skin contaminants. Results are shown in FIG. 8. Only 10 out of 40 data points for the Mie scatter spectrum collected were significantly different ($p<0.05$), but PCA showed that no significant differences exist overall between lotion coated samples and control samples.

Example 7

Determination of Bacterial Species on Skin Surfaces

Figure 7:
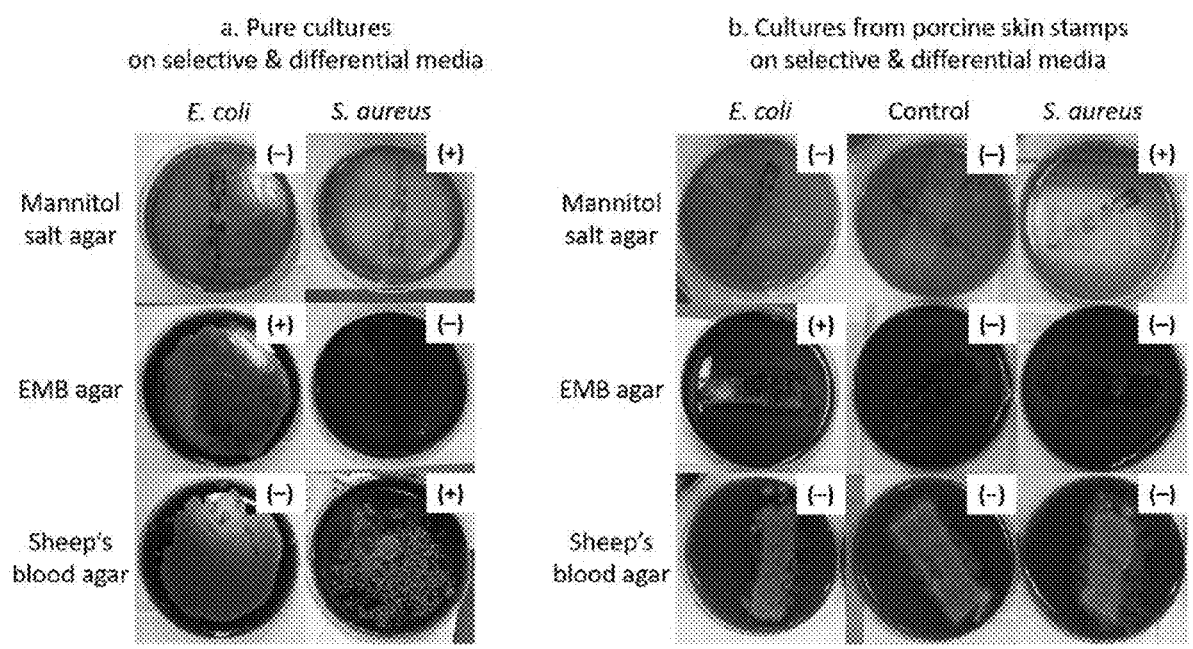
FIG. 7 depicts results from experiments showing that bacteria were shown to be grown successfully on skin surfaces and were identified after growth on the skin surface through selective and differential culture plating prior to detection by an embodiment of the invention.

Using the Materials and Methods in Example 1 and device of Example 2, pure bacterial cultures were cultured on selective and differential media, specifically eosin methylene blue (EMB) agar, mannitol salt agar, and blood agar (TSA+5% sheep's blood). Results are shown in FIG. 7a. *E. coli* did not grow on mannitol salt agar, and grew black with a green metallic sheen on EMB agar, showing that it is in fact *E. coli* growing. *S. aureus* did not grow on EMB agar, grew with beta hemolysis on blood agar, and turned the mannitol salt agar yellow, showing that it is in face *S. aureus* growing.

Following inoculation of bacteria on porcine epidermis samples, the surface was stamped onto selective and differential media. Results are shown in FIG. 7b. Samples inoculated with *E. coli* grew identically to pure cultures of *E. coli*, confirming that the inoculated *E. coli* did in fact grow on the surface of the porcine epidermis. Samples inoculated with *S. aureus* grew identically to pure cultures of *S. aureus*, confirming that the inoculated *S. aureus* did in fact grow on the surface of the porcine epidermis. Samples inoculated with sterile LB (control), showed signs of neither *E. coli* nor *S. aureus* growth to an extent comparable to samples inoculated with these bacteria. For all samples, commensal bacterial present on the skin prior to inoculation also grew, as expected, showing signs of low amounts of *E. coli* and *S. aureus*, which would be expected on skin samples.

Example 8

PCA

While differences were detected through simply scanning the surface of the skin and normalizing to healthy (not infected) skin, these differences become more distinct and allow for species identification when processed using PCA. Data collected from an incident light angle of 110° were excluded from PCA due to the high intensity of scatter at this angle relative to the intensity at all other incident light angles (FIG. 5c). 110° incident light angle is an effective angle for scatter from the topography of the skin (i.e., hair and other imperfections). The standard error of PC1 and PC2 are believed to be larger for human skin samples than those for porcine skin samples due to a combination of the small sample size (due to limited availability of human skin) and the storage of human skin for years in a frozen state and the thawing of the frozen tissue. Although freezing the skin helps to prevent decomposition of the skin, denaturation of the epidermis does occur between freezing and thawing of the tissue.

Example 9

Clinical Use

The device is capable of detection of pathogenic bacteria on skin. In a clinical setting, the photodiode array designed in the above examples is modified to simply scan an area of skin using a digital camera or a smartphone to analyze the presence of an infection in real time. As the data in the above examples were acquired in as little as three seconds, an immediate analysis is performed clinically.

Example 10

Smartphone Application

The device is used in connection with a smartphone application to allow for immediate and non-destructive diagnosis of skin infection in a harmless, painless, and contact-free manner at regular time points. For example, one smartphone is used as a light source utilizing its white LED flash, and the other as a scattering detector utilizing its camera, while the angular positioning is determined utilizing the smartphone's inner gyro sensor. Another example is a smartphone attachments allowing for the filtering and aiming of the white LED flash of the smartphone to act as the light source, or to collect scatter with an angular photodiode array attachment. With the invention, patients can monitor infection at home and be alerted to seek medical attention as soon as an infection begins. For example, the developed technology is used in areas where immediate access to a physician is not possible, so infection can be diagnosed before it is able to become tissue or life threatening infection.

Example 11

Normalization to Control Sample

Variations seen in the presented data are likely due to the presence of commensal bacteria on skin. Skin has high numbers of non-pathogenic bacteria; this system does pick up signals from these commensal bacteria. Variation due to commensal bacteria is reduced in this study by normalizing data to control samples. In a clinical setting, data are normalized to an area of healthy skin to reduce variation due to natural, healthy bacteria presence.

Example 12

Materials and Methods

Bacterial Species Selection

Three bacterial species were tested to span a range of sizes, shapes, and Gram stains (which alter refractive index). *S. aureus* was selected as a Gram positive, small, spherical common wound infection pathogen. *E. coli* was selected as a Gram negative, medium, rod-shaped common wound infection pathogen. *Salmonella typhimurium* was selected to compare to *E. coli*. *E. coli* and *S. typhimurium* are both Gram negative, rod-shaped bacteria, but *S. typhimurium* is slightly larger, so it was selected to determine if similar bacterial species could be differentiated by the device design.

Mie Scatter Simulations

MiePlot v4.2.11 was used to simulate the expected Mie scatter trends of lipid particles, which can be found in the dermis, and bacteria. The following parameters were used to conduct simulations: lipid particle radius=10 μm and refractive index=1.46, *E. coli* particle radius=2.5 μm (hydrodynamic dimensions of 5 μm×1 μm), *S. aureus* particle radius=0.5 μm, *S. typhimurium* particle radius=2.5 μm, for all bacteria refractive index=1.40, for all simulations refractive index of the medium (water)=1.33, wavelength=650 nm, and size distribution was assumed to follow a normal distribution with 10% standard deviation.

Mie scatter simulations were also conducted to select the appropriate light source wavelength by varying the wavelength of the light source from 475 nm to 1400 nm while simulating the Mie scatter of *E. coli*.

Angular Stage Design

An angular photodiode array and tissue stage were created using Solidworks 2014 x64 Edition and 3D printed in ABS. The photodiode array is a semi-circle (radius=25 mm) with an LED insertion point perpendicular to the tissue sample and photodiode insertion points at 10° increments from 10° to 80° of backscatter from the tissue. The tissue stage fits a standard microscope slide to center the tissue below the angular photodiode array. The angular photodiode array height relative to the tissue stage is adjustable, so that the surface of each tissue sample is analyzed despite variations in tissue thickness.

Circuit Design

The 650 nm LED is powered by the 5 V output of an Arduino Mega 2560 microcontroller. The outputs from eight PIN photodiodes in photovoltaic mode are collected individually by the same Arduino Mega 2560. The output of each photodiode is amplified through two gain stages using LM324 quad op-amps to amplify current outputs and the gain is optimized for each angle of detection (Table 1).

Study Design

Porcine dermis samples were split into four groups based on inoculation; Escherichia coli, Staphylococcus aureus, Salmonella typhimurium, or a control of sterile LB-Miller. Mie scatter spectra were collected from each tissue sample at three locations, to ensure that scatter collected was representative of the entire surface. Samples were randomly assigned an inoculum and researchers were not blinded.

Bacteria Solutions

E. coli K12 (Sigma-Aldrich, St. Louis, Mo., USA), S. aureus (ZeptoMetrix, Buffalo, N.Y., USA), and S. typhimurium (ZeptoMatrix, Buffalo, N.Y., USA) were individually cultured in lysogeny broth (LB) Miller's formula (Molecular Biologicals International Inc, Irvine, Calif., USA) at 37° C. for 8 hours.

Tissue Sample Preparation

Porcine skin (University of Arizona Food Products and Safety Laboratory, Tucson, Ariz., USA) was acquired immediately following slaughter. Hair was shaved from the skin and the epidermis was removed via mechanical dissection, exposing the dermis. Samples were cut into rectangles of approximately 1.5 cm by 5 cm and inoculated with 150 μL of either bacteria or LB-Miller, which was spread across the surface evenly. Samples were sealed with Parafilm M (Bemis Flexible Packaging, Oshkosh, Wis., USA) and incubated for 8 hours at 37° C.

Figure 3:
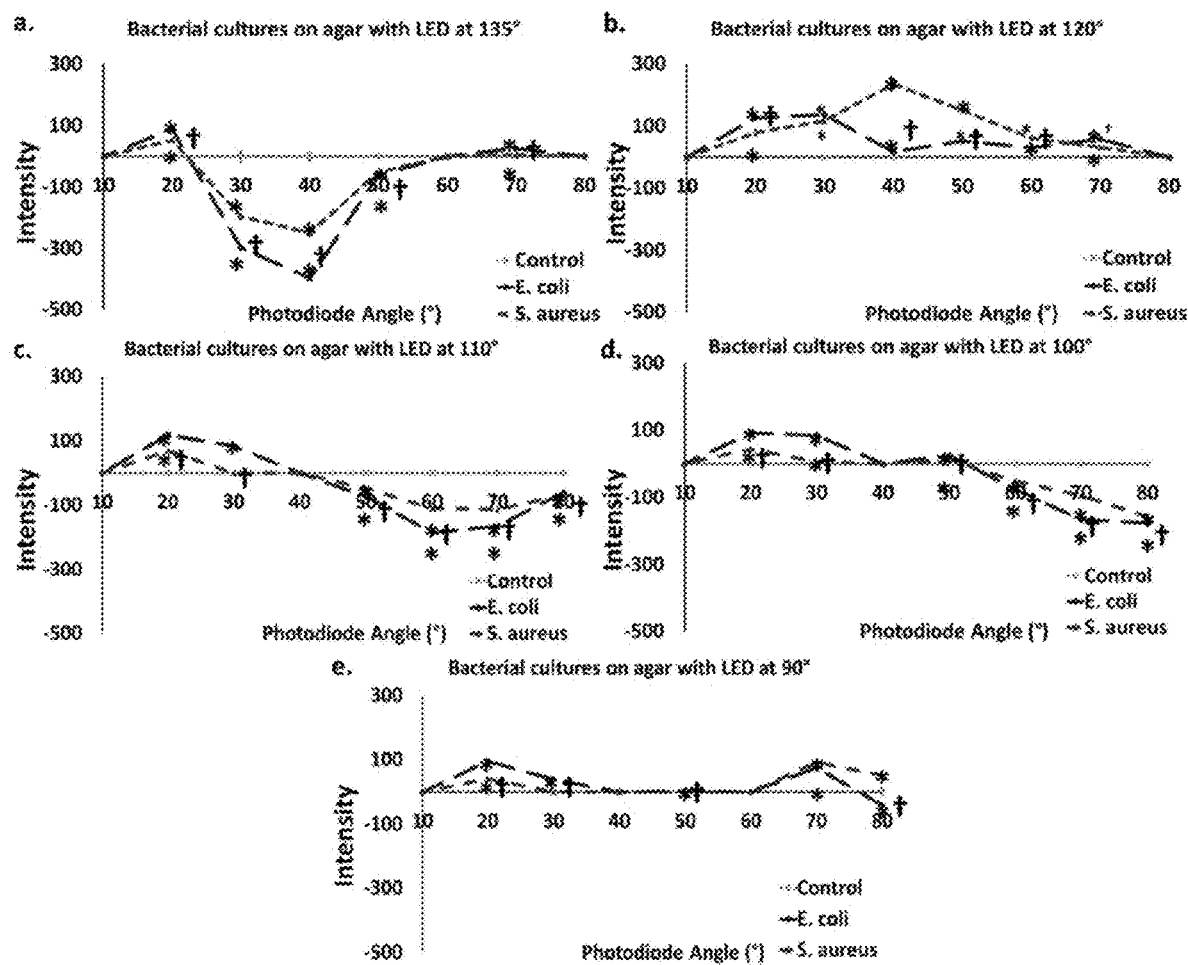
FIG. 3 depicts an example device design. a) The complete photodiode array used for data collection. The array is height adjustable to ensure analysis at the surface of each individual sample. A 650 nm LED illuminates the sample and Mie scatter spectra are detected by photodiodes at increments of 10° from 10° to 80° relative to the tissue surface. The incident angle of the LED is adjustable through individual attachments, due to space constraints on this miniaturized device. b) Each of the five attachments used to change the incident light angle. All five attachments have identical sizes and photodiode locations, with the only difference being the angle at which the LED is held. Using these attachments, the incident light angle can be changed between 90°, 100°, 110°, 120°, and 135°. c) Mie scatter simulations used to determine an effective wavelength to use for the light source within this device. Simulations were conducted based off of parameters for *E. coli* and specifications of the device designed. Based on these simulations, a 650 nm light source was selected as the incident wavelength.
Figure 4:
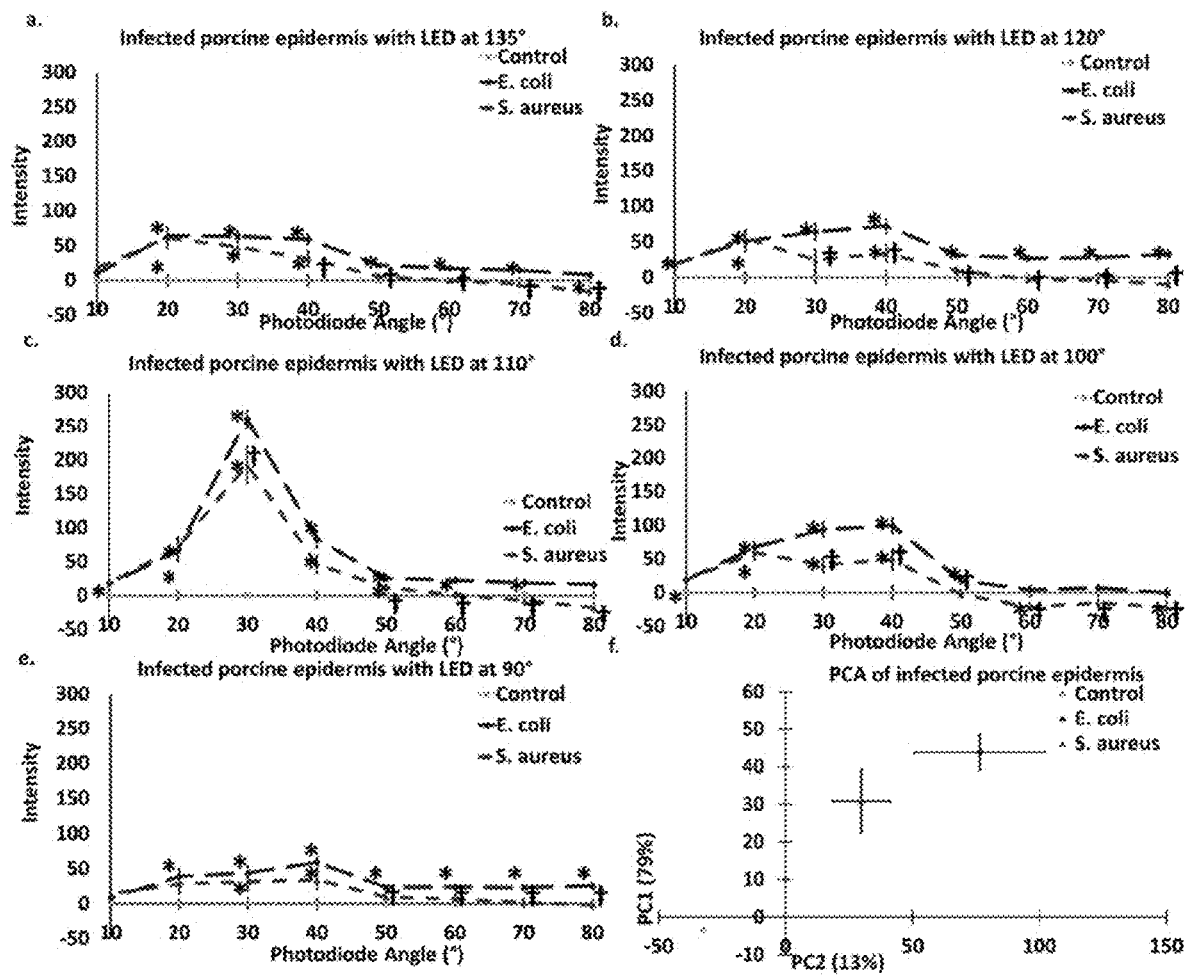
FIG. 4 depicts examples of identification of bacteria in a pure culture using an embodiment of the invention. a-e) Data were obtained from the photodiode array designed by scanning LB agar either sterile or with an inoculation of *E. coli* or *S. aureus*. Incident light angle was changed for each of the five data sets; 135° (a), 120° (b), 110° (c), 100° (d), and 90° (e). At each individual incident light angle, significant differences result between bacterial inoculation and control samples as well as between each species of inoculation; *E. coli* or *S. aureus*. The trend changes as the incident light angle changes, and distinct differences are maintained despite changing trends with changing incident angles. One data point is considered to be the average of 12 readings from each photodiode (3 s scan). Each of five agar samples was scanned at three unique locations for 3 s at each location. Error bars represent standard error of the mean. * is shown to the left side of each data point indicating significant difference ($p<0.05$) between *E. coli* vs. control samples or between *S. aureus* vs. control samples. † is shown to the right side of each data point indicating significant difference ($p<0.05$) between *E. coli* vs. *S. aureus* samples.

The dermis was exposed by shaving the hair and mechanically dissecting away the epidermis of porcine skin samples (FIG. 3). Successful mechanical dissection to expose the dermis was confirmed via light microscopy by confirming that no remnants of the epidermis remained on the surface of the tissue sample and no noticeable cuts in the dermis surface existed.

Mie Scatter Detection

Directly following incubation, samples were transferred to a standard microscope slide and scanned using the angular photodiode array described above. Each tissue sample was analyzed at three locations. Photodiode readings were averaged over 3 s at each location (readings collected every 250 ms, 12 readings averaged). Standard error was calculated for the average of the three locations analyzed on each tissue sample.

Data Analysis and Statistics

Data were analyzed via principal component analysis (PCA) (The Unscrambler v9.7). Error bars represent the standard error of the mean over three analysis locations on each tissue sample. Each study group consisted of 3 individual tissue samples with three locations analyzed on each sample. Two-way Student's t-test assuming equal variance was used to determine statistical significance ($p \leq 0.05$).

Example 13

Device Design

The individual components (FIG. 9a) and the device as assembled (FIG. 9b) are shown, both through computer-aided design models (Solidworks 2014 x64 Edition). The height of the angular photodiode array is adjustable in order to align the focal point of the device with the surface of the tissue, despite variation in tissue thickness from sample to sample.

Example 14

Light Source

Figure 9:
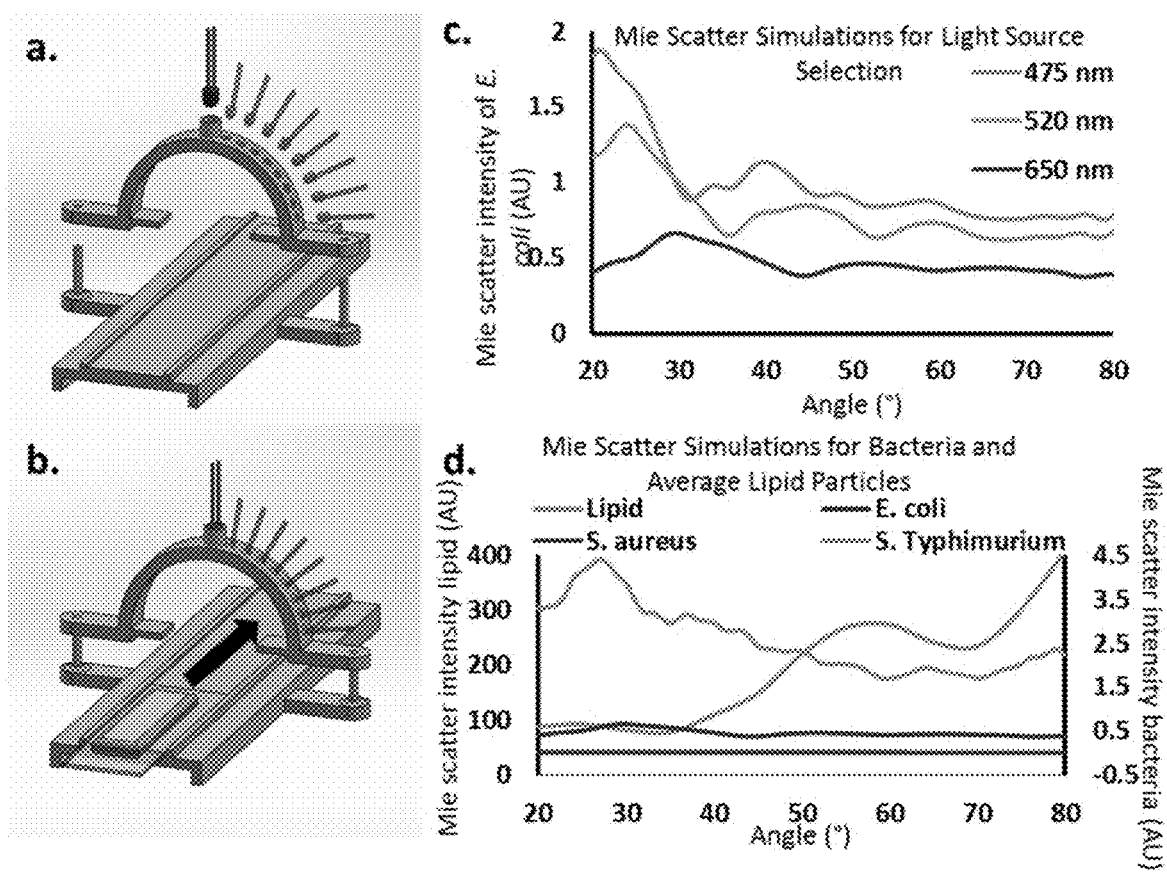
FIG. 9 depicts an embodiment of the invention's device design and projected Mie scatter spectra. a) A computer-aided design of the 3D printed device showing all individual parts. b) A computer-aided design of the 3D printed device showing the final assembly of the device. The tissue sample is loaded into the device on a standard microscope slide by sliding the slide along the track shown. c) Mie scatter simulations used to determine a wavelength LED to use for this device. The Mie scatter trends show an expected peak at 30° for a 650 nm light source. A 650 nm LED was determined to be effective for this device due to this peak, which is relatively high intensity and outside of the 10°-200° range where large intensity variations are observed due to tissue topography.

Using the Materials and Methods in Example 12 and device of Example 13, Mie scatter simulations were conducted to determine an effective light source for bacterial detection from a wound surface, where lipid particles would be present (FIG. 9c). Mie scatter simulations were performed for E. coli (see parameters above) and wavelength was varied from 475 nm to 1400 nm. NIR and IR wavelengths (750 nm, 1000 nm, and 1400 nm) were not considered due to the lower intensity Mie scatter compared to that from visible wavelengths. UV wavelengths were not considered due to their bactericidal capability and the dangers they present to human skin. Due to skin topography and hair follicle presence, large variability was observed in detection at 10° and 20°, so wavelengths with major peaks at these angles were eliminated as possibilities (475 nm and 520 nm). Considering these factors, a wavelength of 650 nm was chosen as an effective light source, which has an expected peak of 30°. Based on this wavelength, simulations for Mie scatter trends for bacteria and lipid particles present in the dermis of skin are shown in FIG. 9d.

Example 15

Device Circuitry

Figure 10:
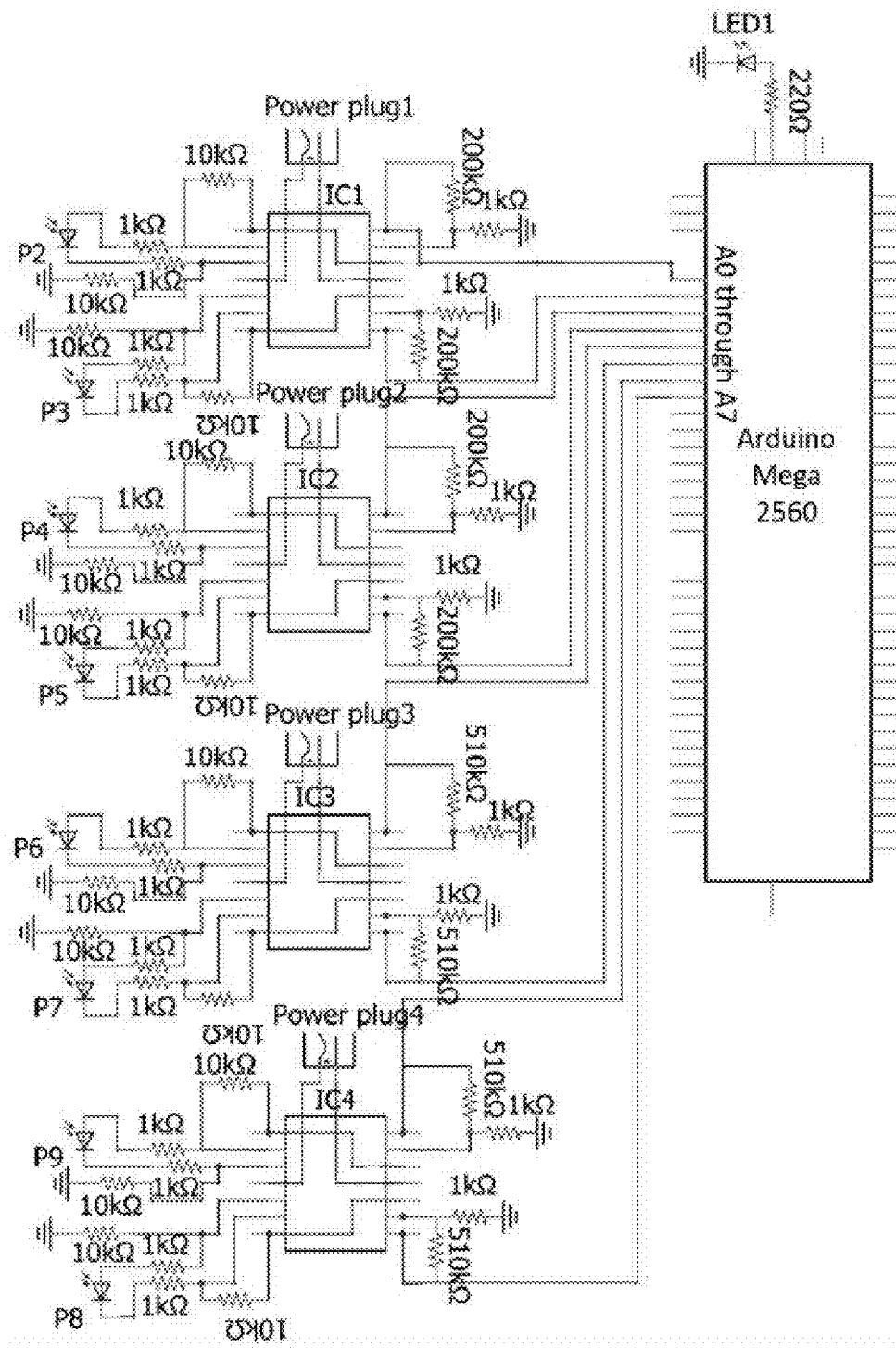
FIG. 10 is a schematic diagram of the circuitry used for an embodiment of the invention. The photodiodes and the LED are housed inside of the 3D printed device that is described. The accompanying circuitry is used to send data to the Arduino Mega 2560 shown. The data are then transferred to a computer by the Arduino Mega 2560 for analysis.
Figure 11:
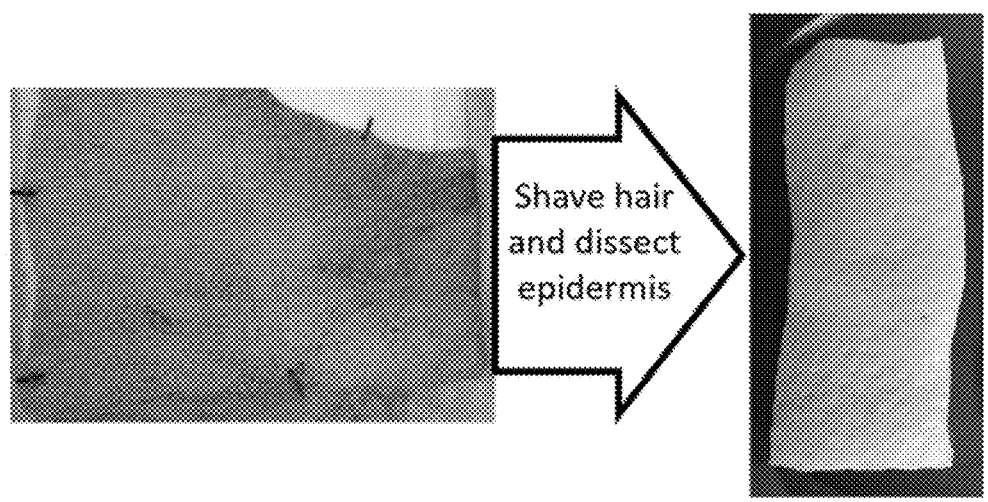
FIG. 11 is a graphical explanation of the processing of porcine skin samples used in experiments using an embodiment of the invention. Porcine skin was collected immediately following slaughter. Hair was shaved from the surface of the skin. The skin was stretched on a surface and a scalpel was used to mechanically dissect away the epidermis, exposing the dermis. Samples were then cut into approximately 1.5 cm×5 cm tissue samples. Tissue samples were rinsed to remove excess hair, loose epidermis, and dirt that was initially on the surface of the skin then inoculated with either a bacterial inoculation or sterile LB. Once processed and inoculated, tissue samples were considered wound models.

Using the Materials and Methods in Example 12 and device of Examples 13-14, the gain was optimized for each photodiode based on maximizing the dynamic range for each individual angle of detection (Table 1). The gain was determined based on the maximum intensity of scatter detected at each angle of detection from alternative porcine skin samples inoculated with E. coli, S. aureus, S. typhimurium, or sterile LB to maximize the dynamic range of the device. The device circuitry based on the optimized gain is shown in FIG. 10. The gain can be changed based on optimizing to different pathogens or purposes.

TABLE 1

| Angle specific gains for all photodiodes | | | |
| --- | --- | --- | --- |
| Photodiode angle | Gain stage 1 | Gain stage 2 | Total gain |
| 80° | 10 | 200 | 2000 |
| 70° | 10 | 200 | 2000 |
| 60° | 10 | 200 | 2000 |
| 50° | 10 | 200 | 2000 |
| 40° | 10 | 510 | 5100 |
| 30° | 10 | 510 | 5100 |
| 20° | 10 | 510 | 5100 |
| 10° | 10 | 510 | 5100 |

Example 16

Mie Scatter Detection from Wound Model

Using the Materials and Methods in Example 12 and device of Examples 13-15, bacteria were grown on porcine dermis to simulate the infection of a wound, where the dermis would be exposed. No obvious visual differences could be seen between samples with different inoculations.

Figure 12:
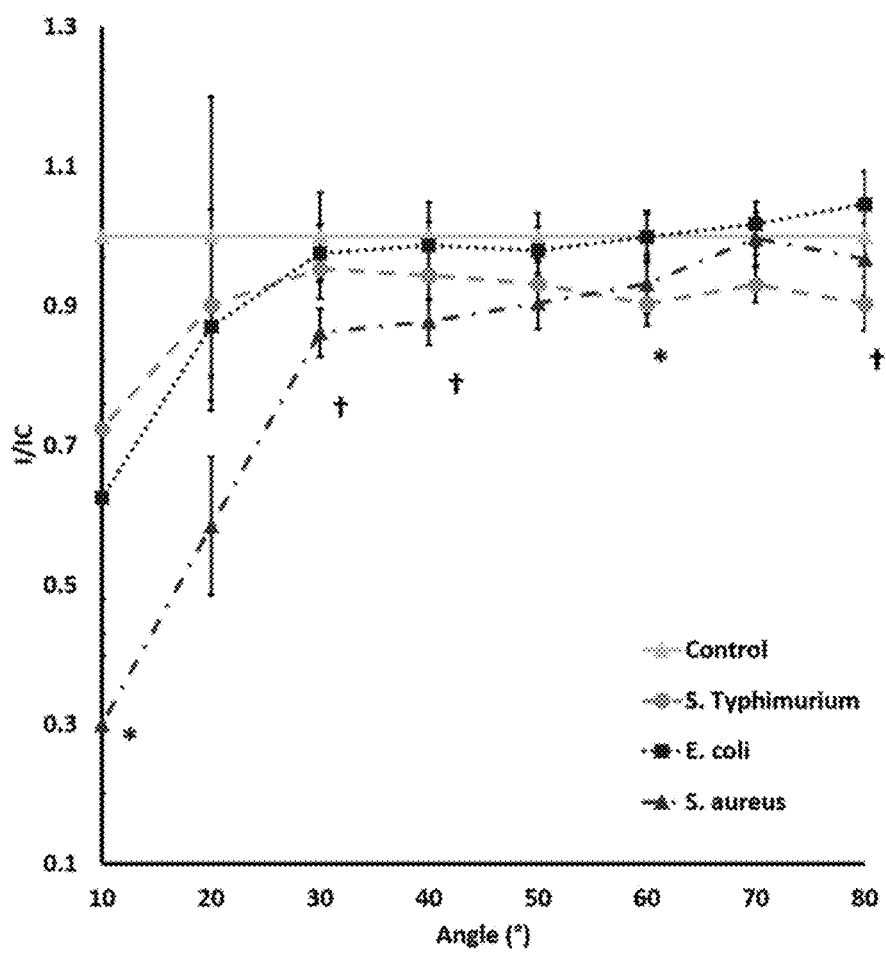
FIG. 12 depicts Mie scatter spectra collected from the surface of porcine dermis samples using an embodiment of the invention. All spectra were normalized to that of control samples by dividing I by IC. Through normalization, the device was able to detect the presence of pathogenic bacteria despite background signal from commensal bacteria on the tissue surface. *=significant differences compared to control samples, †=significant difference compared to *E. coli* inoculated samples, based on $p≤0.05$ being considered significant.

Wound models with different bacterial inoculations resulted in unique Mie scatter spectra detected. FIG. 12 shows the Mie scatter spectra collected after normalizing all spectra collected to control (no inoculation) tissue samples. Significant differences are show in FIG. 12 with p≤0.05 considered significant. The spectra obtained appear to be a combination of the expected Mie scatter spectra of both lipids and each bacterial inoculation (FIG. 9d). The dermis is known to contain lipid molecules and it has been previously shown that bacteria aggregate around lipid molecules [50] which explains the complexities in the Mie scatter spectra.

Figure 13:
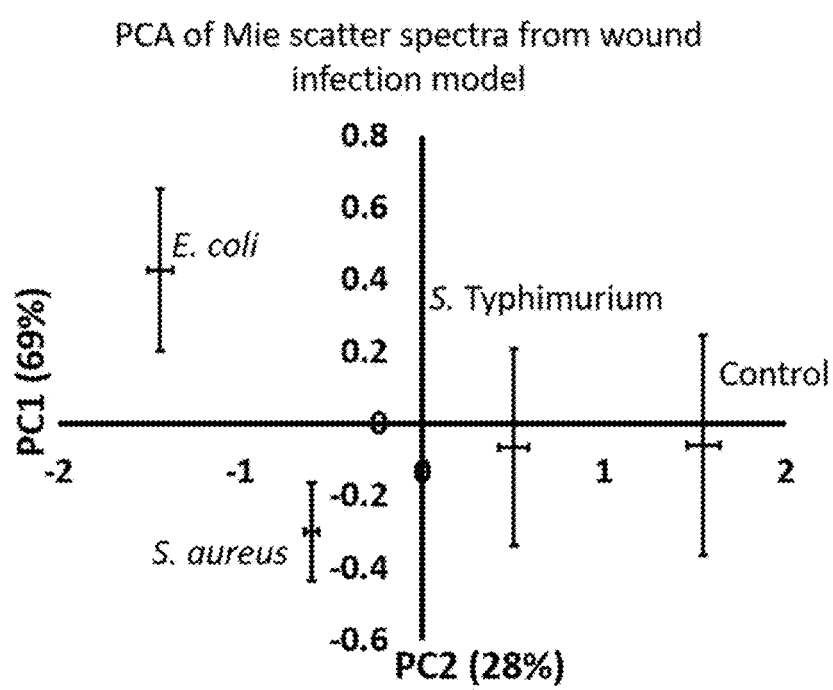
FIG. 13 depicts principal component analysis of the Mie scatter spectra collected from porcine dermis samples scanned with an embodiment of the invention. Principal component 1 (PC1) accounts for 69% of the data collected and PC2 accounts for a further 28%, totaling 97% of the data collected accounted for in just two principal components. Significant differences existed between all experimental groups in PC1 and significant differences exist between *E. coli* and *S. aureus* in PC2 ($p≤0.05$). The device can detect both the presence of pathogenic bacteria on a tissue surface (infection) and the specific species of pathogenic bacteria present on the tissue surface. Each data point represents the average of 12 data points (3 s scan) averaged over three locations on each of three tissue samples.

PCA was performed on the resulting Mie scatter spectra to summarize differences observed between bacterial species (FIG. 13). Significant differences were present between all groups based on principal component 1 (PC1) and between E. coli and S. aureus for PC2 (p≤0.05). PC1 accounts for 69% of the data collected and PC2 accounts for 28%; in total 97% of the data collected is accounted for in just two principal components. The significant differences observed between each species of bacteria and between bacterial inoculation and control samples, show that the device can detect both the presence of a bacterial infection and the species of bacteria responsible for the infection.

The differences detected between each bacterial inoculation were detected in the presence of natural, commensal bacteria present on the surface of the skin by normalizing the Mie scatter spectra collected from "infected" tissue (bacterial inoculation) to that of "non-infected" tissue (control samples) to reduce the impact of the Mie scatter spectra of the natural, commensal bacteria.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

In some embodiments, the numbers expressing quantities of ingredients, properties such as molecular weight, reaction conditions, and so forth, used to describe and claim certain embodiments of the application are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

In some embodiments, the terms "a" and "an" and "the" and similar references used in the context of describing a particular embodiment of the application (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. No language in the specification should be construed as indicating any non-claimed element essential to the practice of the application.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

BIBLIOGRAPHY

1. Grice, E. A. et al. A diversity profile of the human skin microbiota. *Genome Res.* 18, 1043-1050 (2008).
2. Grice, E. A. et al. Topographical and temporal diversity of the human skin microbiome. *Science* 324, 1190-1192 (2009).
3. Grice, E. A. & Segre, J. A. The skin microbiome. *Nature Rev. Microbiol.* 9, 244-253 (2011).
4. Roth, R. R. & James, W. D. Microbiology of the skin: resident flora, ecology, infection. *J. Am. Acad. Dermatol.* 20, 367-390 (1989).
5. Schommer, N. N. & Gallo, R. L. Structure and function of the human skin microbiome. *Trends Microbiol.* 21, 660-668 (2013).
6. Cardona, A. F. & Wilson, S. E. Skin and soft-tissue infections: a critical review and the role of telavancin in their treatment. *Clin. Infect. Dis.* 61, S69-S78 (2015).

7. Ki, V. & Rotstein, C. Bacterial skin and soft tissue infections in adults: a review of their epidemiology, pathogenesis, diagnosis, treatment and site of care. *Can. J. Infect. Dis.* 19, 173-184 (2008).
8. Bernard, P. Management of common bacterial infections of the skin. *Curr. Opin. Infect Dis.* 21, 122-128 (2008).
9. Bisno, A. L. & Stevens, D. L. Streptococcal infections of skin and soft tissues. *New Engl. J. Med.* 334, 240-245 (1996).
10. Ray, G. T., Suaya, J. A. & Baxter, R. Microbiology of skin and soft tissue infections in the age of community-acquired methicillin-resistant *Staphylococcus aureus*. *Diagn. Microbiol. Infect. Dis.* 76, 24-30 (2013).
11. Sladden, M. J. & Johnston, G. A. Common skin infections in children. *BMJ* 329, 95 (2004).
12. T. R. Dargaville, B. L. Farrugia, J. A. Broadbent, S. Pace, Z. Upton, N. H. Voelcker, Sensors and imaging for wound healing: A review. *Biosens. Bioelectron.* 41, 30-42 (2013).
13. B. A. Lipsky, A. R. Berendt, P. B. Cornia, J. C. Pile, E. J. G. Peters, D. G. Armstrong, H. G. Deery, J. M. Embil, W. S. Joseph, A. W. Karchmer, M. S. Pinzur, E. Senneville, 2012 Infectious Diseases Society of America Clinical Practice Guideline for the Diagnosis and Treatment of Diabetic Foot Infections. *Clin. Infect. Dis.* 54, e132-e173 (2012).
14. D. L. Stevens, A. L. Bisno, H. F. chambers, E. P. Dellinger, E. J. C. Goldstein, S. L. Gorbach, J. V. Hirchmann, S. L. Kaplan, J. G. Montoya, J. C. Wade, Practice Guidelines for the Diagnosis and Management of Skin and Soft Tissue Infections: 2014 Update by the Infectious Diseases Society of America. *Clin. Infect. Dis.* 59, e10-e52 (2014).
15. A. Markova, E. N. Mostow, US Skin Disease Assessment: Ulcer and Wound Care. *Dermatol. Clin.* 30, 107-111 (2012).
16. C. K. Sen, G. M. Gordilla, S. Roy, R. Kirsner, L. Lambert, T. K. Hunt, F. Gottrup, G. C. Gurtner, M. T. Longtaker, Human Skin Wounds: A Major and Snowballing Threat to Public Health and the Economy. *Wound Rep. Reg.* 17, 763-771 (2009).
17. Iyer, S. & Jones, D. H. Community-acquired methicillin-resistant *Staphylococcus aureus* skin infection: a retrospective analysis of clinical presentation and treatment of local outbreak. *J. Am. Acad. Dermatol.* 50, 854-858 (2003).
18. Uthayakumar, S., Nandwani, R., Drinkwater, T., Nayagam, A. T. & Darley, C. R. The prevalence of skin disease in HIV infection and its relationship to the degree of immunosuppression. *Br. J. Dermatol.* 137, 595-598 (1997).
19. Cogen, A. L., Nizet, V. & Gallo, R. L. Skin microbiota: a source of disease or defence? *Br. J. Dermatol.* 158, 442-455 (2007).
20. DeLeo, F. R., Otto, M, Kreiswirth, B. N. & Chambers, H. F. Community-associated methicillin-resistant *Staphylococcus aureus*. *Lancet* 375, 1557-1568 (2010).
21. Pardos de la Gandara, M. et al. Molecular types of methicillin-resistant *Staphylococcus aureus* and methicillin-sensitive *S. aureus* causing skin and soft tissue infections and nasal colonization, identified in community health centers in New York City. *J. Clin. Microbiol.* 53, 2648-2658 (2015).
22. A. A. L. M. Rondas, J. M. G. A. Schols, R. J. G. Halfens, E. E. Stobberingh, Swab Versus Biopsy for the Diagnosis of Chronic Infected Wounds. *Adv. Skin Wound Care.* 26(5), 211-219 (2013).
23. M. Reddy, S. S. Gill, W. Wu, S. R. Kalkar, P. A. Rochon, Does This Patient Have an Infection of a Chronic Wound?. *JAMA.* 307(6), 605-611 (2012).
24. Center for Disease Control and Prevention. *National Diabetes Statistics Report: Estimates of Diabetes and Its Burden in the United States,* 2014. Atlanta, Ga.: US Department of Health and Human Services (2014).
25. S. P. Pendsey, Understanding Diabetic Foot. *Int. J. Diabetes Dev. Ctries.* 30(2), 75-79 (2010).
26. K. Pickwell, V. Siersma, M. Kars, J. Apelqvist, K. Bakker, M. Edmonds, P. Holstein, A. Jirkovska, E. Jude, D. Mauricio, A. Piaggesi, G. R. Tennvall, H. Reike, M. Spraul, L. Ucciolo, V. Urbancic, K. van Acker, J. van Baal, N. Schaper, Predictors of Lower-Extremity Amputation in Patients With an Infected Diabetic Foot Ulcer. *Diabetes Care.* 38(5), 852-857 (2015).
27. R. G. Frykerg, W. A. Marston, M. Cardinal, The Incidence of Lower-Extremity Amputation and Bone Resection in Diabetic Foot Ulcer Patients Treated with a Human Fibroblast-Derived Dermal Substitute. *Adv. Skin Wound Care.* 28(1), 17-20 (2015).
28. A. L. Brubaker, J. L. Rendon, L. Ramirez, M. A. Choudhry, E. J. Kovacs, Reduced Neutrophil Chemotaxis and Infiltration Contributes to Delayed Resolution of Cutaneous Wound Infection with Advanced Age. *J. Immunol.* 190, 1746-1757 (2013).
29. E. A. Azzopardi, E. Azzopardi, L. Camilleri, J. Villapalos, D. E. Boyce, P. Dziewulski, W. A. Dickson, I. S. Whitaker, Gram Negative Wound Infectin in Hospitalized Adult Burn Patients-Systematic Review and Metanalysis. *PLoS ONE.* 9(4), e95042 (2014).
30. A. Fournier, O. Pantet, S. Guerid, P. Eggimann, J. L. Pagani, J. P. Revelly, P. M. Hauser, O. Marchetti, S. Fontanella, I. Letovanec, F. Ravat, M. M. Berger, A. Pannatier, P. Voirol, Y. A. Que, Effective Treatment of Invasive *Aspergillus fumigatus* Infection Using Combinations of Topical and Systemic Antifunals in a Severely Burned Patient. *J. Burn Care Res.* 36(2), e85-e89 (2015).
31. E. Korol, K. Johnston, N. Waser, F. Sifakis, H. S. Jafri, M. Lo, M. H. Kyaw, A Systematic Review of Risk Factors Associated with Surgical Site Infections among Surgical Patients. *PLoS ONE.* 8(12), e83743 (2013).
32. G. Ortega, D. S. Rhee, D. J. Papandria, J. Yang, A. M. Ibrahim, A. D. Shore, M. A. Makary, F. Abdullah, An Evaluation of Surgical Site Infections by Wound Classification System Using the ACS-NSQIP. *J Surg. Res.* 174(1), 33-38 (2012).
33. S. Zehtabchi, A. Tan, K. Yadav, A. Badawy, M. Lucchesi, The Impact of Wound Age on the Infection Rate of Simple Lacerations Repaired in the Emergency Department. *Injury, Int. J. Care Injured.* 43, 1793-1798 (2012).
34. Stevens, D. L. et al. Practice guidelines for the diagnosis and management of skin and soft-tissue infections: 2014 update by the Infectious Diseases Society of America. *Clin. Infect. Dis.* 59, e10-e52 (2014).
35. Kong, H. H. Skin microbiome: genomics-based insights into the diversity and role of skin micrbiomes. *Trends Mol. Med.* 17, 320-328 (2011).
36. Banada, P. P. et al. Label-free detection of multiple bacterial pathogens using light-scattering sensor. *Biosens. Bioelectron.* 24, 1685-1692 (2009).
37. Singh, A. K. et al. Laser optical sensor, a label0free on-plate *Salmonella enterica* colony detection tool. *mBio* 5, e01019-13 (2014).

38. Tang, Y. et al. Light scattering sensor for direct identification of colonies of *Escherichia coli* serogroups O26, O45, O103, O111, O121, O145 and O157. *PLOS ONE* 9, e105272 (2014).
39. Liang, P. S., Park, T. S. & Yoon, J. Y. Light scattering based detection of food pathogens, in: Lu, R. (Ed.), *Light Scattering Technology for Food Property, Quality and Safety Assessment*. Taylor & Francis: Abingdon, pp. 429-444 (2016).
40. T. S. Park, W. Li, K. E. McCracken, J. Y. Yoon, Smartphone Quantifies *Salmonella* from Paper Microfluidics. *Lab Chip*. 13, 4832-4840 (2013).
41. P. S. Liang, T. S. Park, J. Y. Yoon, Rapid and Reagentless Detection of Microbial Contamination Within Meat Utilizing a Smartphone-Based Biosensor. *Sci. Rep.* 4, 5953 (2014).
42. S. Cho, T. S. Park, T. G. Nahapetian, J. Y. Yoon, Smartphone-Based, Sensitive μPAD Detection of Urinary Tract Infection and Gonorrhea. *Biosens. Bioelectron.* 74, 601-611 (2015).
43. Pei's book chapter
44. P. P. Banada, K. Huff, E. Bae, B. Rajwa, A. Aroonnual, B. Bayraktar, A. Adil, J. P. Robinson, E. D. Hirleman, A. K. Bhunnia, Label-Free Detection of Multiple Bacterial Pathogens using Light-Scattering Sensor. *Biosens. Bioelectron.* 24, 1685-1692 (2009).
45. A. K. Singh, A. M. Bettasso, E. Bae, B. Rajwa, M. M. Dundar, M. D. Forster, L. Liu, B. Barrett, J. Lovchik, J. P. Robinson, E. D. Hirleman, A. K. Bhunia, Laser Optical Sensor, a Label-Free On-Plate *Salmonella enterica* Colony Detection Tool. *mBio.* 5(1), e01019-13 (2014).
46. Y. Tang, H. Kim, A. K. Singh, A. Aroonnual, E. Bae, B. Rajwa, P. M. Fratamico, A. K. Bhunia, Light Scattering Sensor for Direct Identification of colonies of *Escherichia coli* Serogroups O26, O45, O103, O111, O121, O145, and O157. *PLoS ONE.* 9(8), e105272 (2014).
47. Liang, P. S., Park, T. S. & Yoon, J. Y., Rapid and reagentless detection of microbial contamination within meat utilizing a smartphone-based biosensor. *Sci. Rep.* 4, 5953.
48. Cho, S., Park, T. S., Nahapetian, T. G. & Yoon, J. Y., Smartphone-based, sensitive μPAD detection of urinary tract infection and gonorrhea. *Biosens. Bioelectron.* 74, 601-611 (2015).
49. Park, T. S., Li, W., McCracken, K. E. & Yoon, J. Y. Smartphone quantifies *Salmonella* from paper microfluidics. *Lab Chip* 13, 4832-4840 (2013).
50. P. S. Liang, T. S. Park, J. Y. Yoon, "Rapid and reagentless detection of microbial contamination within meat utilizing a smartphone-based biosensor," *Sci. Rep.*, vol. 4, pp. 5953, August, 2014. doi: 10.1038/srep05953.

What is claimed is:

1. A device for analysis of one or more pathogens in or on a human or animal tissue through collecting and analyzing Mie scattering intensities over a range of detection angles, wherein the device comprises a light source and a photodiode array, or one or more photomultiplier tubes, or optionally a smartphone camera, and a means for collecting and analyzing said Mie scattering intensities selected from the group consisting of a smartphone, a tablet and a computer;
wherein said light source, and photodiode array, or said one or more photomultiplier tubes, are arranged on a semi-circular stage;
wherein said device collects said Mie scatter intensities over a range of eight scattering detection angles between 10° to 135° relative to the tissue; and
wherein said device detects backscatter intensity patterns from the surface of said tissue surface without collecting images;
wherein optionally the incident angle of the light source is adjustable, and
wherein said device detects changes in Mie scatter patterns based on particle size and concentration to detect one or more pathogens on the surface of said tissue surface.

2. The device of claim 1, wherein the device further comprises a stage to accommodate a sample of said tissue on a microscope slide.

3. The device of claim 1, wherein the light source is a red LED with peak irradiation wavelength from 600 nm to 700 nm.

4. The device of claim 3, wherein the light source is a 650 nm red LED.

5. The device of claim 1, wherein the angle of said light source is adapted to change from 90° perpendicular to the tissue surface to 135°.

6. The device of claim 1, wherein the device is adapted to analyze the tissue at one or more incident light angles.

7. The device of claim 1, wherein said photodiode array is a plurality of photodiodes.

8. The device of claim 7, wherein said photodiode array simultaneously collects light scatter intensities off of said tissue at multiple scatter angles to obtain a Mie scattering intensities.

9. The device of claim 8, wherein the detection angles are in 10°-30° increments from 10° to 80° relative to the tissue.

10. A method for diagnosing a tissue infection, wherein the method comprises
placing a tissue in proximity to a device such that the photodiode array or photomultiplier tubes of the device are in a suitable position with respect to the tissue to conduct a Mie scattering determination;
determining the Mie scattering intensities over a range of back scattering angles, with the device; and
comparing the Mie scattering to a standard Mie scattering;
wherein difference in Mie scattering is indicative of a tissue infection;
wherein said device comprises a light source and a photodiode array, or one or more photomultiplier tubes, or optionally a smartphone camera, and a means for collecting and analyzing said Mie scattering intensities selected from the group consisting of a smartphone, a tablet and a computer;
wherein said light source, and photodiode array, or said one or more photomultiplier tubes, are arranged on a semi-circular stage;
wherein said device collects said Mie scatter intensities over a range of at least eight scattering detection angles between 10° to 80° relative to the tissue; and
wherein said device detects backscatter intensity patterns from the surface of said tissue surface without collecting images;
wherein optionally the incident angle of the light source is adjustable, and
wherein said device detects changes in Mie scatter patterns based on particle size and concentration to detect one or more pathogens on the surface of said tissue surface.

11. A method for identifying one or more pathogen types in an infected tissue wherein the method comprises
placing a tissue in proximity to a device such that the photodiode array or photomultiplier tubes of the device are in a suitable position with respect to the tissue to conduct a Mie scattering determination;

determining the Mie scattering intensities over a range of back scattering angles with the device; and comparing the Mie scattering to a standard Mie scatterings;

wherein specific Mie scatterings correspond to a specific pathogen type wherein said device comprises a light source and a photodiode array, or one or more photomultiplier tubes, or optionally a smartphone camera, and a means for collecting and analyzing said Mie scattering intensities selected from the group consisting of a smartphone, a tablet and a computer;

wherein said light source, and photodiode array, or said one or more photomultiplier tubes, are arranged on a semi-circular stage;

wherein said device collects said Mie scatter intensities over a range of at least eight scattering detection angles between 10° to 80° relative to the tissue; and wherein said device detects backscatter intensity patterns from the surface of said tissue surface without collecting images;

wherein optionally the incident angle of the light source is adjustable, and wherein said device detects changes in Mie scatter patterns based on particle size and concentration to detect one or more pathogens on the surface of said tissue surface.

12. The method of claim 11, wherein the specific pathogen type is one or more species of bacteria, fungi, or viruses, or any combination thereof.

* * * * *